United States Patent
Deorazio et al.

(10) Patent No.: US 6,919,377 B2
(45) Date of Patent: Jul. 19, 2005

(54) CYCLOHEXYLAMINE DERIVATIVE AS SUBTYPE SELECTIVE NMDA RECEPTOR ANTAGONISTS

(75) Inventors: Russell Joseph Deorazio, Schenectady, NY (US); Sham Shridhar Nikam, Ann Arbor, MI (US); Ian Leslie Scott, Delanson, NY (US); Brian Alan Sherer, Ballston Spa, NY (US); Lawrence David Wise, Ann Arbor, MI (US)

(73) Assignee: Warner Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 10/258,721

(22) PCT Filed: Apr. 24, 2001

(86) PCT No.: PCT/US01/13176
§ 371 (c)(1),
(2), (4) Date: Oct. 25, 2002

(87) PCT Pub. No.: WO01/81295
PCT Pub. Date: Nov. 1, 2001

(65) Prior Publication Data
US 2003/0236286 A1 Dec. 25, 2003

Related U.S. Application Data
(60) Provisional application No. 60/199,762, filed on Apr. 26, 2000.

(51) Int. Cl.[7] ...................... C07D 213/02; A61K 31/44
(52) U.S. Cl. .................. 514/617; 514/357; 514/619; 514/621; 546/329; 564/161; 564/163; 564/169; 564/170
(58) Field of Search ................... 514/357, 617, 514/619, 621; 546/329; 564/161, 163, 169, 170

(56) References Cited

FOREIGN PATENT DOCUMENTS

| | | |
|---|---|---|
| DE | 4438020 | 2/1996 |
| EP | 0507291 | 7/1992 |
| EP | 0940387 | 8/1999 |
| EP | 0982026 | 1/2000 |
| WO | 0000197 | 6/2000 |

OTHER PUBLICATIONS

PCT International Search Report, PCT/US01/13176.
Cantarelli et al., "Fenilcicloesilammine E Derivati Nota III—3— e 4–fenilcicloesilammine mono– e disostituite all'azoto Loro attivita anestetica locale e pressoria", Il Farmaco. Ed. Sc., vol. 25, No. 4, 1970, pp. 248–294.

*Primary Examiner*—Zinna Northington Davis
(74) *Attorney, Agent, or Firm*—Suzanne M. Harvey; Mehdi Ganjeizadeh; David R. Kurlandsky

(57) ABSTRACT

Described are compounds of Formula I and Formula II and their pharmaceutically acceptable salts. The compounds of Formulas I and II are antagonists of NMDA receptor channel complexes useful for treating cerebral vascular disorders such as, for example, cerebral ischemia, cardiac arrest, stroke, and Parkinson's disease.

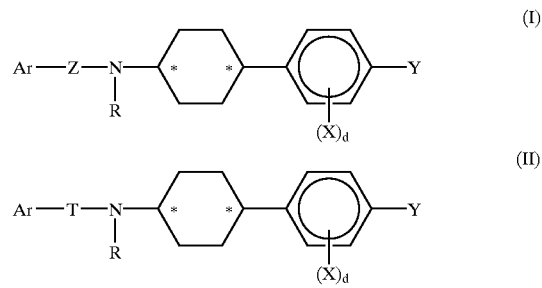

10 Claims, No Drawings

CYCLOHEXYLAMINE DERIVATIVE AS SUBTYPE SELECTIVE NMDA RECEPTOR ANTAGONISTS

This application is a 371 application of PCT/US01/13176 filed Apr. 24, 2001, which claims the benefit of priority to U.S. provisional application Ser. No. 60/199,762, filed Apr. 26, 2000.

FIELD OF THE INVENTION

The invention pertains to (phenylcyclohexyl)amine derivatives as sub type selective N-Methyl-D-Aspartate Antagonists (NMDA).

BACKGROUND OF THE INVENTION

Over excitation of NMDA receptor channel complexes on postsynaptic neurons following excessive release of glutamic acid from synaptosomes and glutamic acid from synaptosomes and glial cells results in excessive calcium ion influx into the neuronal cells, which leads to their death. This is believed to occur under ischemic or hypoxic conditions such as stroke, hypoglycemic, cardiac arrest and physical trauma. An NMDA receptor antagonist might be therapeutically useful because it may minimize damage of the central nervous system induced by ischemic or hypoxic conditions. The NMDA receptor channel complex consists of at least three binding domains including a glutamic acid (or NMDA) recognition site, a channel blocking binding site, and a strychnine-insensitive glycine binding type. Physiologically, a blockade of at least one of these sites terminates the channel opening of the NMDA receptor to prevent a calcium ion influx (Nagata R. et al., *J. Med. Chem.*, 1994;37:3956–3968.

Excessive excitation of NMDA receptor channel complexes by neurotransmitters may be responsible for the loss of neurons in cerebral vascular disorders such as cerebral ischemia or cerebral infarction resulting in a range of conditions such as thromboembolic or hemorrhagic stroke, cerebral vasospasm, hypoglycemia, cardiac arrest, status epilepticus, perinatal asphyxia, anoxia, such as from near drowning, pulmonary surgery and cerebral trauma, as well as lathyrism, Alzheimer's disease, and Huntington's disease. Such conditions likewise suggest the use of agents that may act as antagonists in the receptors identified above may lead to treatment of amyotrophic lateral sclerosis (ALS), schizophrenia, parkinsonism, epilepsy, anxiety, pain, and drug addiction (PCT/EPO 94/01492 having publication number WO#94/26747, Watjen et al., published Nov. 24, 1994).

L-glutamic acid, L-aspartic acid and a number of other closely related amino acids have the ability to activate neurons in the nervous system and therefor the vast majority of excitatory neurons in the mammalian CNS. Interaction with glutamic acid mediated neurotransmission is considered a useful approach in the treatment of neurological and psychiatric diseases (Jacobsen et al., WO#94/26746, published Nov. 24, 1994).

Excitatory amino acid receptor antagonists that block NMDA receptors are recognized for usefulness in the treatment of a variety of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease (Klockgether T., Turski L., *Ann Neurol.* 1993;34:585–593), human immunodeficiency virus (HIV) related neuronal injury, amyotrophic lateral sclerosis (ALS), Alzheimer's disease (Francis P. T., Sims N. R., Procter A. W., Bowen D. M., *J. Neurochem.,* 1993;60(5):1589–1604) and Huntington's disease [see Lipton S., *TINS,* 1993;16:(12):527–532; Lipton S., Rosenberg P. A., *New Eng. J. Med* 1994;330(9): 613–622 and Bigge C. F., *Biochem. Pharmacol.* 1993;45:1547–1561 and references cited therein]. NMDA receptor antagonists may also be used to prevent tolerance to opiate analgesia or to help control withdrawal symptoms from addictive drugs (Eur P., *Application* 488:959A).

Many of the properties of native NMDA receptors are seen in recombinant homomeric NR receptors. These properties are altered by the NR2 subunits. Recombinant NMDA receptors expressed in Xenopus Oocytes have been studied by voltage-clamp recording, and have been found to exhibit developmental and regional expression of the mRNAs encoding NMDA receptor subunits. Electrophysiological assays were utilized to characterize the actions of compounds at NMDA receptors expressed in Xenopus Oocytes. The compounds were assayed at four subunit combinations at cloned rat NMDA receptors, corresponding to three putative NMDA receptor subtypes (Moriyoshi et al., *Nature,* 1991;354:31–37; Monyer et al., *Science,* 1992:256:1217–1221; Kutsuwada et al., *Nature,* 1992;358:3641; Sugihara et al., *Biochem. Biophys. Res. Commun.,* 1992;185:826–832).

Expression cloning of the first NMDA receptor subunit, NMDAR1 (NR1) in Nakanishi's lab in 1991 provided an initial view of the molecular structure of the NMDA receptor (Moriyoshi, supra., 1991). There are several other structurally related subunits (NMDAR2A through NMDAR2D) that join NR1 in heteromeric assemblies to form the functional ion channel complex of the receptor (*Ann Rev. Neurosci.,* 1994;17:31–108). The molecular heterogeneity of NMDA receptors implies a future potential for agents with subtype selective pharmacology.

SUMMARY OF THE INVENTION

Compounds of Formula I

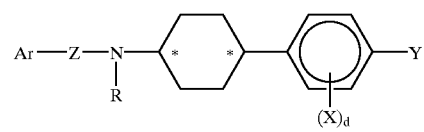

I or a pharmaceutically acceptable salt thereof
wherein:
Ar is aryl or heteroaryl, which heteroaryl is from 5 to 14 atoms having from 1 to 2 heteroatoms selected from the group consisting of N, O, and S;

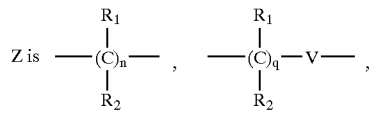

-continued

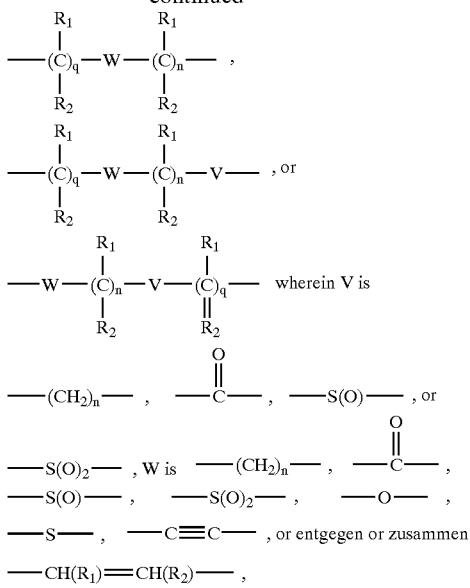

d is an integer of from 1 to 2,
n is an integer from 1 to 6,
q is an integer from 0 to 6,
$R_1$ and $R_2$ are independently selected from the group consisting of hydrogen, alkyl, OH, hydroxyalkyl, aminoalkyl, aralkyl, or $N(R_4)(R_5)$ wherein $R_4$ and $R_5$ are independently selected from hydrogen, alkyl, aralkyl, heteroaryl, heteroarylalkyl, aminoalkyl, hydroxyalkyl, and thioalkyl;
R is hydrogen, alkyl, $C(O)P_6$, $C(O)OR_6$, $C(O)NHR_6$, aralkyl, hydroxyalkyl, aminoalkyl, amino(hydroxy)alkyl, carboxyalkyl, or OH wherein $R_6$ is alkyl or aralkyl;
Y is a hydrogen bond donor group;
X is independently selected from hydrogen or an electron withdrawing group; and
* denotes cis or trans or a mixture thereof.

The invention also relates to compounds of Formula II

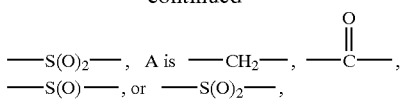

or a pharmaceutically acceptable salt thereof
wherein:
Ar is aryl or heteroaryl, which heteroaryl is from 5 to 14 atoms having from 1 to 2 heteroatoms selected from N, O, and S;

T is $(A)_{0-1}$—N($R_3$)—$(U)_{0-1}$—(C($R_1$)($R_2$))$_t$— or $(A)_{0-1}$—N($R_3$)—(C($R_1$)($R_2$))$_t$—$(U)_{0-1}$—,

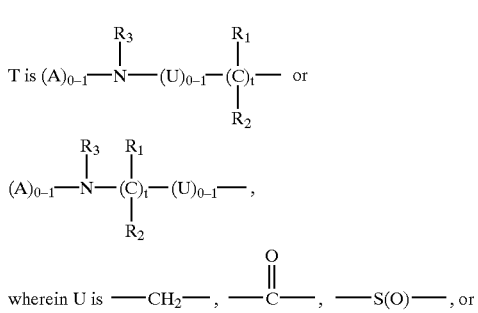

wherein U is —CH$_2$—, —C(=O)—, —S(O)—, or
—S(O)$_2$—, A is —CH$_2$—, —C(=O)—,
—S(O)—, or —S(O)$_2$—, d is an integer from 1 to 2,
t is an integer from 1 to 3,
$R_1$ and $R_2$ are independently selected from hydrogen, alkyl, OH, hydroxyalkyl, aminoalkyl, thioalkyl, aryl, aralkyl, heteroaryl, heteroarylalkyl, guanidinyl, (aminocarbonyl) alkyl-, carboxyalkyl-, (methylthio)-alkyl-, or $N(R_4)(R_5)$ wherein $R_4$ and $R_5$ are independently selected from hydrogen, alkyl, aralkyl, heteroaryl, heteroarylalkyl, ureidoalkyl, aminoalkyl, hydroxyalkyl, or thioalkyl,
$R_3$ is hydrogen, alkyl, OH, or aralkyl,
R is hydrogen, alkyl, $C(O)R_6$, $C(O)OR_6$, $C(O)NHR_6$, aralkyl, hydroxyalkyl, aminoalkyl, amino(hydroxy)alkyl, carboxyalkyl, or OH wherein $R_6$ is alkyl or aralkyl;
Y is a hydrogen bond donor group;
X is independently selected from hydrogen or an electron withdrawing group; and
* denotes cis or trans or a mixture thereof.

The invention is also concerned with a pharmaceutical composition useful for treating disorders responsive to the selective blockade of N-methyl-D-aspartate receptor subtypes utilizing the compounds of Formula I or Formula II and the pharmaceutically acceptable salts thereof, optionally disorders as stroke, cerebral ischemia, trauma, hypoglycemia, neurodegenerative disorders, anxiety, depression, migraine headache, convulsions, aminoglycoside antibiotics-induced hearing loss, psychosis, glaucoma, CMV retinitis, opioid tolerance or withdrawal, chronic pain, or urinary incontinence.

The invention is also concerned with a method of treating disorders responsive to the selective blockade of the N-methyl-D-aspartate receptor subtypes in a mammal suffering thereof which comprises administering in unit dosage form, at least one compound represented by Formula I or Formula II above or its pharmaceutically acceptable salts thereof

DETAILED DESCRIPTION OF THE INVENTION

In the compounds of the present invention preferred are compounds of Formula I or pharmaceutically acceptable salts thereof wherein Y is a hydrogen bond donor group para to cyclohexyl on the phenyl ring selected from the group consisting of OH, heterocycle, which heterocycle is a carboxylic acid or an amide isostere, $NH_2$, SH, and $NHR_7$, wherein $R_7$ is alkyl, aralkyl, $C(O)R_8$, $C(O)OR_8$, $C(O)NHR_8$, $SO_2R_8$, or $SO_2NHR_8$ and $R_8$, is alkyl, aralkyl, or aryl; and
X is independently selected from hydrogen or an electron withdrawing group selected from the group consisting of halogen, nitro, cyano, aminoalkyl, $CF_3$, $C(O)CH_3$, and haloalkyl.

More preferred are compounds of Formula I or pharmaceutically acceptable salts thereof wherein Ar is unsubstituted or substituted phenyl;
Y is a hydrogen bond donor group selected from the group consisting of OH, heterocycle, which heterocycle is a carboxylic acid or an amide isostere, $NH_2$, SH, and $NHR_7$, wherein $R_7$ is alkyl, aralkyl, $C(O)R_8$, $C(O)OR_8$, $C(O)NHR_8$, $SO_2R_8$, or $SO_2NHR_8$, and $R_8$ is alkyl, aralkyl, or aryl;
X is independently selected from hydrogen or an electron withdrawing group selected from the group consisting of halogen, nitro, cyano, aminoalkyl, $CF_3$, $C(O)CH_3$, and haloalkyl; and
* denotes trans.

Still more preferred are compounds of Formula I or pharmaceutically acceptable salts thereof wherein Ar is unsubstituted or substituted phenyl; Z is as defined above and further a group whereby Ar and the nitrogen atom in Formula I are separated by from 2 to 4 atoms; Y is a hydrogen bond donor group selected from the group consisting of OH, heterocycle, which heterocycle is a carboxylic acid isostere, $NH_2$, SH, and $NHR_7$, wherein $R_7$ is alkyl, aralkyl, $C(O)R_8$, $C(O)OR_8$, $C(O)NHR_8$, $SO_2R_8$, or $SO_2NHR_8$, and $R_8$ is alkyl, aralkyl, or aryl;
X is hydrogen or an electron withdrawing group selected from the group consisting of halogen, nitro, cyano, alkyl, $CF_3$, $C(O)CH_3$, and haloalkyl; and
* denotes trans.

Still more preferred are compounds of Formula I or pharmaceutically acceptable salts thereof where Ar is unsubstituted or substituted phenyl;

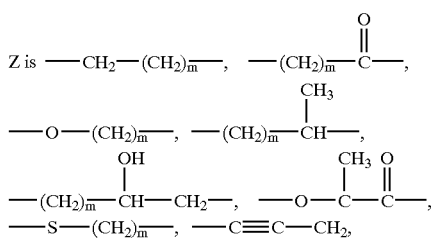

or —C≡C—(CH$_2$)$_2$—
wherein m is an integer 1 to 3;
R is hydrogen, methyl, or $C(O)CH_3$;
Y is a hydrogen bond donor group, which group is OH;
X is hydrogen; and
* denotes trans.

Most preferred is a compound selected from those listed below:
4-{4-[Ethyl(3-phenylpropyl)amino]cyclohexyl}phenol;
4-{4-[Isopropyl(3-phenylpropyl)amino]cyclohexyl}phenol;
cis-4-[4-(4-Phenylbutylamino)cyclohexyl]phenol;
trans-4-[4-(4-Phenylbutylamino)cyclohexyl]phenol;
cis-4-[4-(3-Phenylpropylamino)cyclohexyl]phenol;
trans-4-[4-(3-Phenylpropylamino)cyclohexyl]phenol;
4-(4-Phenethylaminocyclohexyl)phenol;
trans-4-(4-Benzylaminocyclohexyl)phenol;
cis-4-(4-Benzylaminocyclohexyl)phenol;
trans-4-{4-[2-(4-Fluorophenyl)ethylamino]cyclohexyl}phenol;
cis-4-{4-[2-(4-Fluorophenyl)ethylamino]cyclohexyl}phenol;
trans-4-[4-(1-Methyl-3-phenylpropylamino)cyclohexyl]phenol;
cis-4-[4-(1-Methyl-3-phenylpropylamino)cyclohexyl]phenol;
trans-4-[4-((R)-1-Methyl-3-phenylpropylamino)cyclohexyl]phenol;
trans-4-[4-((S)-1-Methyl-3-phenylpropylamino)cyclohexyl]phenol;
trans-4-{4-[(Pyridin-3-ylmethyl)amino]cyclohexyl}phenol;
cis-4-{4-[(Pyridin-3-ylmethyl)amino]cyclohexyl}phenol;
trans-4-{4-[2-(4-Methoxyphenyl)ethylamino]cyclohexyl}phenol;
cis-4-{4-[2-(4-Methoxyphenyl)ethylamino]cyclohexyl}phenol;
4-[4-(5-Phenylpentylamino)cyclohexyl]phenol;
trans-4-[4-((R)-1-Hydroxymethyl-2-phenylethylamino)cyclohexyl]phenol;
cis-4-[4-((R)-1-Hydroxymethyl-2-phenylethylamino)cyclohexyl]phenol;
trans-4-[4-(2-Phenoxyethylamino)cyclohexyl]phenol;
cis-4-[4-(2-Phenoxyethylamino)cyclohexyl]phenol;
trans-4-[4-(3-Pyridin-4-ylpropylamino)cyclohexyl]phenol;
cis-4-[4-(3-Pyridin-4-ylpropylamino)cyclohexyl]phenol;
4-[4-((S)-1-Methyl-2-phenylethylamino)cyclohexyl]phenol;
trans-4-[4-(3-Pyridin-3-ylpropylamino)cyclohexyl]phenol;
cis-4-[4-(3-Pyridin-3-ylpropylamino)cyclohexyl]phenol;
trans-4-[4-(3-Pyridin-2-ylpropylamino)cyclohexyl]phenol;
cis-4-[4-(3-Pyridin-2-ylpropylamino)cyclohexyl]phenol;
N-Benzyl-N-[4-(4-hydroxyphenyl)cyclohexyl]acetamide;
N-[4-(4-Hydroxyphenyl)cyclohexyl]-N-(3-phenylpropyl)acetamide;
N-[4-(4-Hydroxyphenyl)cyclohexyl]-N-(3-phenylpropyl)carbamic acid methyl ester;
N-Benzyl-N-[4-(4-hydroxyphenyl)cyclohexyl]carbamic acid methyl ester;
4-{4-[Methyl-(3-phenylpropyl)amino]cyclohexyl}phenol;
N-[4-(4-Hydroxyphenyl)cyclohexyl]-3-phenylpropionamide;
N-[4-(4-Hydroxyphenyl)cyclohexyl]-2-methyl-2-phenoxypropionamide;
4-[4-(3-Phenylprop-2-ynylamino)cyclohexyl]phenol;
4-[4-(2-Phenylsulfanylethylamino)cyclohexyl]phenol;
4-{4-[3-(4-Methoxyphenyl)propylamino]cyclohexyl}phenol;
4-{4-[Benzyl(3-phenylpropyl)amino]cyclohexyl}phenol;
4-{4-[methyl(2-phenoxyethyl)amino]cyclohexyl}phenol; and
2-Aminomethyl-4-{4-[ethyl(3-phenylpropyl)amino]cyclohexyl}phenol.

Preferred are compounds of Formula II or pharmaceutically acceptable salts thereof wherein Y is a hydrogen bond donor group para to cyclohexyl on the phenyl ring selected from the group consisting of OH, heterocycle, which heterocycle is a carboxylic acid or an amide isostere, $NH_2$, SH and $NHR_7$, wherein $R_7$ is alkyl, aralkyl, $C(O)R_8$, $C(O)OR_8$, $C(O)NHR_8$, $SO_2R_8$, or $SO_2NHR_8$ and $R_8$ is alkyl, aralkyl, or aryl; and X is independently selected from hydrogen or an electron withdrawing group selected from the group consisting of halogen, nitro, cyano, aminoalkyl, $CF_3$, $C(O)CH_3$, and haloalkyl.

More preferred are compounds of Formula II or pharmaceutically acceptable salts thereof wherein:
Ar is unsubstituted or substituted phenyl;
Y is a hydrogen bond donor group selected from the group consisting of OH, heterocycle, which heterocycle is a carboxylic acid or an amide isostere, $NH_2$, SH, and $NHR_7$, wherein $R_7$ is alkyl, aralkyl, $C(O)R_8$, $C(O)OR_8$, $C(O)NHR_8$, $SO_2R_8$, or $SO_2NHR_8$, and $R_8$ is alkyl, aralkyl, or aryl;
X is independently selected from hydrogen or an electron withdrawing group selected from the group consisting of halogen, nitro, cyano, aminoalkyl, $CF_3$, $C(O)CH_3$, and haloalkyl; and
* denotes trans.

Still more preferred are compounds of Formula II or pharmaceutically acceptable salts thereof wherein:

Ar is unsubstituted or substituted phenyl;

Ar and the nitrogen atom bearing R are separated by 3 or 4 atoms;

Y is a hydrogen bond donor group selected from the group consisting of OH, heterocycle, which heterocycle is a carboxylic acid or an amide isostere, $NH_2$, SH and $NHR_7$, wherein $R_7$ is alkyl, aralkyl, $C(O)R_8$, $C(O)OR_8$, $C(O)NHR_8$, $SO_2R_8$, or $SO_2NHR_8$, and $R_8$ is alkyl, aralkyl, or aryl;

X is independently selected from hydrogen or an electron withdrawing group selected from the group consisting of halogen, nitro, cyano, aminoalkyl, $CF_3$, $C(O)CH_3$, and haloalkyl; and

* denotes trans.

Still more preferred are compounds of Formula II or pharmaceutically acceptable salts thereof wherein:

Ar is unsubstituted or substituted phenyl;

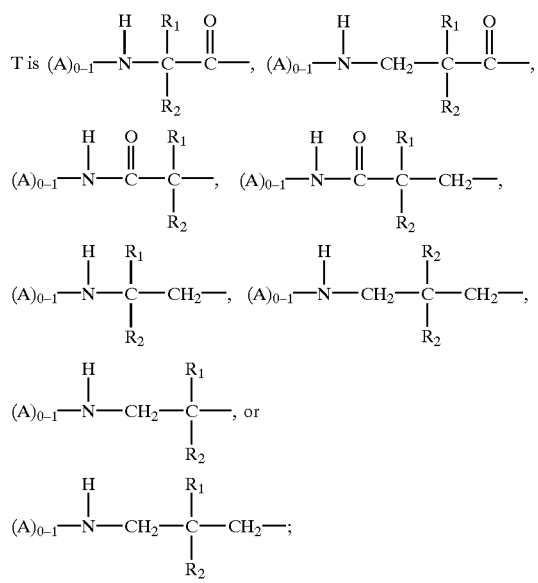

R is hydrogen or methyl;

Y is a hydrogen bond donor group, which group is OH;

X is hydrogen; and

* denotes trans.

A preferred material is: 4-[4-(2-Phenylaminoethylamino)cyclohexyl]phenol.

Another preferred compound is that of Formula III

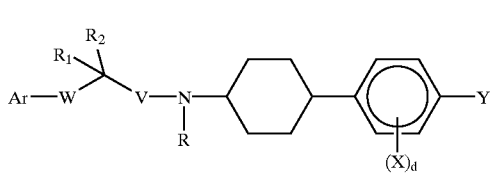

with the substituents as described above.

Another preferred compound is that of Formula IV

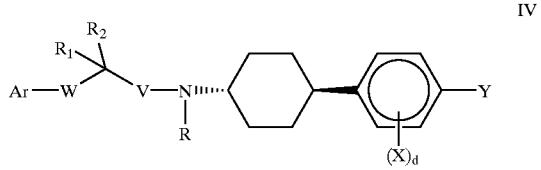

with the substituents as described above.

In compounds of Formulas I–III, cis materials are also preferred.

It is to be appreciated that the Y group is a hydrogen bond donor group that is attached at one and only one carbon atom of the phenylene ring.

The term "alkyl" means a straight or branched hydrocarbon radical having from 1 to 12 carbon atoms unless otherwise specified, also known as a $C_1$–$C_{12}$ alkyl, and includes, for example, methyl, ethyl, 1-propyl, and 2-propyl, 1-butyl, 2-butyl, 2-methyl-1-propyl, 1,1-dimethylethyl, 1-pentyl, 2-pentyl, 3-pentyl, 2,2-dimethylpropyl, 1-hexyl, 2-hexyl, 3-hexyl, 4-methyl-1-pentyl, 1-heptyl, 2-heptyl, 3-heptyl, 4-heptyl, 5-methyl-1-hexyl, 1-octyl, 2-octyl, 3-octyl, 4-octyl, 6-methyl-1-heptyl, 5,5-dimethylhexyl, 1-nonyl, 2-nonyl, 1-decyl, 2-decyl, 1-undecyl, 2-undecyl, 1-dodecyl, and 5-dodecyl. Alkyl groups may be unsubstituted or independently substituted by from 1 to 3 substituents selected from F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

Alkyl groups having two or more carbons may optionally contain 1 or 2 sites of unsaturation, the groups being known as alkenyl groups or radicals. Illustrative examples of an alkenyl group or radical having from 2 to 12 carbon atoms, also known as a $C_2$ to $C_{12}$ alkenyl, include ethenyl, 1-propenyl, 2-propenyl, 1-buten-1-yl, 2-buten-1-yl, 1-penten-1-yl, 2-penten-1-yl, 1-penten-3-yl, 1-penten-5-yl, 1-hexen-1-yl, 1-hexen4-yl, 2-hexen-1-yl, 3-hexen-1-yl, 2-octen-3-yl, 5-nonen-2-yl, 4-undecen-4-yl, and 5-dodecen-2-yl.

The term "aryl" means an aromatic carbocyclic ring having from 6 to 10 carbon atoms. Illustrative examples of an aryl group or radical include phenyl, 1-naphthyl, and 2-naphthyl. Aryl groups may be unsubstituted or independently substituted by from 1 to 3 substituents selected from F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

The term "aralkyl" means an aryl-alkyl-group or radical wherein aryl and alkyl have the meanings as defined above. Illustrative examples of an arylalkyl group or radical include benzyl, 4-fluorophenylmethyl, 2-phenylethyl, 3-phenylpropyl, 4-phenylbutyl, 3-methyl-3-phenylpropyl, 1-naphthylmethyl, 1-naphthylethyl, 3-(1-naphthyl)-propyl, 4-(1-naphthyl)-butyl, 4-(2-naphthyl)-butyl, 4-phenylheptyl, and 12-(2-hydroxyphenyl)-dodec-3-yl.

The term "heteroatom" means nitrogen, oxygen, or sulfur.

The term "heteroaryl" means an unsaturated monocyclic group or radical of 5 or 6 atoms, an unsaturated fused bicyclic group or radical of from 8 to 10 atoms, or an unsaturated fused tricyclic group or radical of from 11 to 14 atoms, the cyclic groups having 1 or 2 heteroatoms independently selected from O, N, or S. Illustrative examples of monocyclic heteroaryl include 2- or 3-thienyl, 2- or 3-furanyl, 1-, 2- or 3-pyrrolyl, 1-, 2- or 4-imidazolyl, 1-, 3- or 4-pyrazolyl, 2-, 4- or 5-oxazolyl, 2-, 4- or 5-thiazolyl, 3-, 4- or 5-isoxazolyl, 3-, 4- or 5-isothiazolyl, 2-, 3- or 4-pyridinyl, 3- or 4-pyridazinyl, 2- or 3-pyrazinyl, and 2-, 4- or 5-pyrimidinyl. Illustrative examples of bicyclic heteroaryl include 2-, 3-, 4-, 5-, 6-, 7- or 8-quinolinyl, 1-, 3-, 4-, 5-, 6-, 7- or 8-isoquinolinyl, 1-, 2-, 3-, 4-, 5-, 6- or 7-indolyl, 2-, 3-, 4-, 5-, 6- or 7-benzo[b]thienyl, 2-, 4-, 5-, 6- or 7-benzofuran, 2-, 4 5-, 6- or 7-benzoxazolyl, 2-, 4-, 5-, 6- or 7-benzothiazolyl, and 1-, 2-, 3-, 4-, 5-, 6- or 7-benzimidazolyl. Illustrative examples of tricyclic heteroaryl include 1-, 2-, 3- or 4-dibenzofuranyl, 1-, 2-, 3- or 4-dibenzothienyl and 1-, 2-, 3-, 4-, 5-, 6-, 7-, 8-, or 9-(1,2,3,4-tetrahydroacridinyl). All with the proviso that when Z in Formula I is attached via a heteroatom, Z is attached to a carbon atom of the heteroaryl group or radical. Heteroaryl groups may be unsubstituted or independently substituted by from 1 to 3 substituents selected from F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

As used above, a fused bicyclic group or radical is a group wherein two ring systems share two and only two atoms.

As used above, a fused tricyclic group or radical is a group wherein three ring systems share four and only four atoms.

The term "heteroarylalkyl" means a heteroaryl-alkyl-group or radical wherein heteroaryl and alkyl have the meanings as defined above. Illustrative examples of an heteroarylalkyl group or radical include 4-pyridyl-methyl, (4-fluoroquinolin-2-yl)methyl, 2-(isoxazol-3-yl)ethyl, and 12-(5-chlorothiophen-2-yl)-dodec-3-yl.

The term "halogen" means bromine, chlorine, fluorine or iodine.

The term "aminoalkyl" means an H2N-alkyl-group or radical wherein alkyl has the meaning as defined above, which is a substituted alkyl group or radical containing from 1 to 3 substituents wherein at least one substituent is —NH2.

The term "hydroxyalkyl" means an HO-alkyl-group or radical wherein alkyl has the meaning as defined above, which is a substituted alkyl group or radical containing from 1 to 3 substituents wherein at least one substituent is —OH.

The term "amino(hydroxy)alkyl" means an $H_2N(HO)$-alkyl-group or radical wherein alkyl has the meaning as defined above, which is a substituted alkyl group or radical containing from 2 or 3 substituents wherein at least one substituent is OH and one substituent is —NH2.

The term "(aminocarbonyl)alkyl" means an $H_2NC(O)$-alkyl-group or radical wherein alkyl has the meaning as defined above, which is a substituted alkyl group or radical containing from 1 to 3 substituents wherein at least one substituent is —(O)C—$NH_2$.

The term "thioalkyl" means an HS-alkyl-group or radical wherein alkyl has the meaning as defined above, which is a substituted alkyl group or radical containing from 1 to 3 substituents wherein at least one substituent is —SH.

The term "(methylthio)-alkyl-" means an CH3S-alkyl-group or radical wherein alkyl has the meaning as defined above, which is a substituted alkyl group or radical containing from 1 to 3 substituents wherein at least one substituent is —$SCH_3$.

The term "carboxyalkyl" means an $HO_2C$-alkyl-group or radical wherein alkyl has the meaning as defined above, which is a substituted alkyl group or radical containing from 1 to 3 substituents wherein at least one substituent is —$CO_2H$.

The term "haloalkyl" means a halogen-alkyl-group or radical wherein halogen and alkyl have the meanings as defined above, which is a substituted alkyl group or radical containing from 1 to 3 substituents wherein at least one substituent is selected from F, Cl, Br, or I.

The term "ureidoalkyl" means an $H_2N$—(C=O)—NH-alkyl-group or radical wherein alkyl has the meanings as defined above, which is a substituted alkyl group or radical containing from 1 to 3 substituents wherein at least one substituent is $H_2N$—(C=O)—NH—.

The term "guanidinyl" means an $H_2N$—(C=NH)—NH— group or radical.

The term "hydrogen bond donor groups" means a group or radical selected from OH, heterocycle, which heterocycle is a carboxylic acid or amide isostere $NH_2$, SH, $CH_2$—C(O) $CH_3$, $NHR_7$ wherein $R_7$ is alkyl, aralkyl, $C(O)R_8$, $C(O)OR_8$, $C(O)NHR_8$, $P(O)(O—R_8)_2$, $SO_2R_8$, or SO2NHR8 wherein R8 is alkyl, aralkyl, or aryl. The importance of the hydrogen bond donor group in certain antagonists selective for certain NMDA receptor subunits is known (Chenard B. L., Menniti F. S., Curr. Pharm. Design 1999;5:381–404).

The term "electron withdrawing group" means a group or radical selected from halogen, nitro, cyano, alkyl, $CF_3$, $C(O)CH_3$, $P(O)(O—R_9)_2$, $SO_2$—$R_9$, $SO_2NHR_9$, $C(O)$ NR9R9' wherein $R_9$ is independently selected from $C_1$-$C_6$ alkyl or unsubstituted or substituted phenyl, —(C=NH)— $NH_2$, —(C=NH)—O-alkyl, methoxymethyl, or haloalkyl, wherein the substituents may be F, Cl, Br, I, OH, $NH_2$, SH, CN, $NO_2$, $OCH_3$, $OC(O)CH_3$, $CF_3$, $OCH_2CH_2OH$, NHC(O) $CH_3$, $NHCH_3$, or $N(CH_3)_2$.

The phrase "heterocycle, which heterocycle is a carboxylic acid or an amide isostere" means a 5- or 6-membered monocyclic ring containing from 1 to 4 heteroatoms selected from N, O, and S and providing a hydrogen bond donor moiety selected from NH, OH, and SH. Illustrative examples include the following structures:

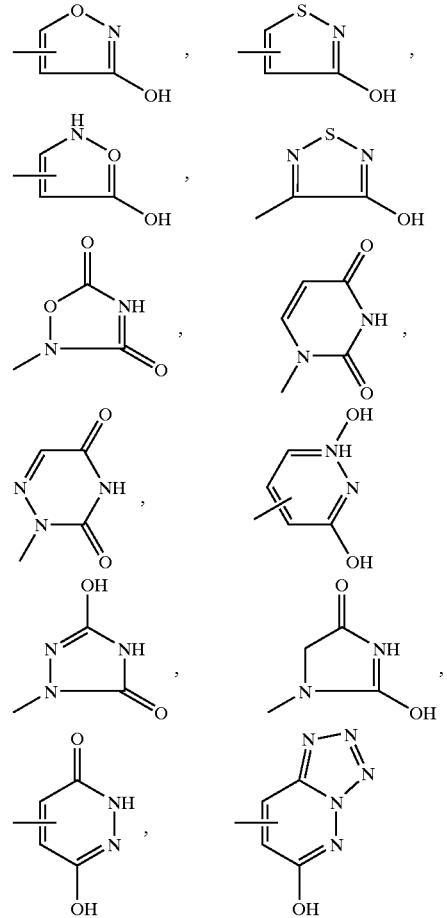

-continued

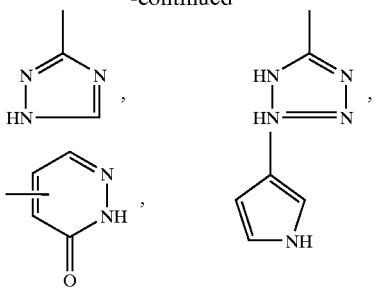

See also Greenwood J. R., Vaccarella G., Cooper H. R., Allan R. D., Johnston G. A. R., *Internet Journal of Chemistry*, 1998;1(Article 38) Chart 4). Additional examples are well-known to the skilled artisan (see, for example, (i) Lipinski C. A., *Annual Reports in Medicinal Chemistry*, 1986;21:Chapter 21, Chapter 27; (ii) Thomber C. W., *Chem. Soc. Rev.*, 1979;8:563; (iii) Burger A., *Progress in Drug Research*, 1991;37:288–371).

The term "entgegen" means the stereoisomerism about a carbon-carbon double bond wherein the highest ranking substituent on each carbon are on opposite sides, which substituent ranking is based on the sequence rules of the Cahn-Ingold-Prelog system (March J., *Advanced Organic Chemistry*, 4th ed., 1992 John Wiley & Sons, New York, pp. 109 and 127 and references cited therein).

The term "zusammen" means the stereoisomerism about a carbon-carbon double bond wherein the highest ranking substituent on each carbon are on the same side, which substituent ranking is based on the sequence rules of the Cahn-Ingold-Prelog system (March J., *Advanced Organic Chemistry*, 4th ed., 1992;109,127; John Wiley & Sons, New York, and references cited therein).

The term "cis" means the stereoisomerism about a carbon-carbon double bond, a monocyclic ring, a fused bicyclic ring, or a bridged bicyclic ring wherein the highest ranking substituent on each of the two carbons of relevance are on the same side, which substituent ranking is based on the sequence rules of the Cahn-Ingold-Prelog system (March J., *Advanced Organic Chemistry*, 4th ed., 1992;109:127–133; John Wiley & Sons, New York, and references cited therein).

The term "trans" means the stereoisomerism about a carbon-carbon double bond, a monocyclic ring, a fused bicyclic ring, or a bridged bicyclic ring wherein the highest ranking substituent on each of the two carbons of relevance are on opposite sides, which substituent ranking is based on the sequence rules of the Cahn-Ingold-Prelog system (March J.,*Advanced Organic Chemistry*, 4$^{th}$ ed., 1992;109,127–133; John Wiley & Sons, New York, and references cited therein).

The terms "cis" or "trans" refers to the relative stereochemistry of the groups attached to the cyclohexyl rings of Formulas I or II at the carbon atoms denoted by "*".

The term "(X)d" means the group X is present 1 or 2 times on the phenylene to which it is attached, which group is independently selected from hydrogen or an electron withdrawing group wherein the electron withdrawing group is as defined above unless otherwise stated. The groups X can be the same or different.

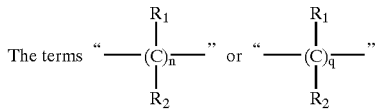

wherein n is an integer of from 1 to 6 and q is an integer of from 0 to 6 mean a chain of from 1 to 6 carbons or from 0 to 6 carbons, respectively, wherein each carbon is independently substituted, which substituents are the groups $R_1$ and $R_2$, wherein $R_1$ and $R_2$ are independently ($R_1$ and $R_2$ in each occurrence can be the same or different) selected from the groups consisting of hydrogen, alkyl, OH, hydroxyalkyl, aminoalkyl, aralkyl, or $N(R_4)(R_5)$ wherein R4 and $R_5$ are independently selected from hydrogen, alkyl, aralkyl, heteroaryl, heteroarylalkyl, aminoalkyl, hydroxyalkyl and thioalkyl, unless otherwise stated. The groups $R_1$ can be the same or different, and the groups $R_2$ can be the same or different.

For purposes of the syntheses of the compounds of the present invention, reactive functional groups present in starting materials, reaction intermediates, or reaction products may be protected during chemical reactions using protecting groups which render the reactive functional groups substantially inert to the reaction conditions (see for example, *Protective Groups in Organic Synthesis*, 2nd ed., Green T. W. and Wuts P. G.: John Wiley & Sons, New York, NY, 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with Zinc.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

Some of the compounds of Formulas I–III are capable of further forming pharmaceutically acceptable acid-addition and/or base salts. All of these forms are within the scope of the present invention.

Pharmaceutically acceptable acid addition salts of the compounds of Formulas I–III include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate and the like and gluconate, galacturonate (see, for example, Berge S. M. et al., "Pharmaceutical Salts," *Journal of Pharmaceutical Science,* 1977;66:1–19).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N-dibenzylethylenediamine, chloroprocaine, choline, diethanolamine, dicyclohexylamine, ethylenediamine, N-methylglucamine, and procaine (see, for example, Berge, supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formulas I–III or a corresponding pharmaceutically acceptable salt of a compound of Formulas I–III.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists or as agents for the treatment of diseases, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

| Tablet Formulation | |
|---|---|
| Ingredient | Amount (mg) |
| 4-[4-(3-Phenylpropylamino)cyclohexyl]phenol | 25 |
| Lactose | 50 |
| Cornstarch (for mix) | 10 |
| Cornstarch (paste) | 10 |
| Magnesium stearate (1%) | 5 |
| Total | 100 |

The 4-[4-(3-Phenylpropylamino)cyclohexyl]phenol, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of disease caused by over excitation of NMDA receptor channel complexes.

The compounds of the present invention can be prepared according to the various synthetic schemes that follow. Protecting groups may be used when appropriate throughout many of the schemes. Although specifically noted in certain schemes, the appropriate use and choice of protecting groups is well-known by one skilled in the art, and is not limited to the specific examples below. It is also understood that such groups not only serve to protect chemically reactive sites, but also to enhance solubility or otherwise change physical properties. A good general reference for protecting group preparation and deprotection is "Protective Groups in Organic Synthesis" by Theodora Green, supra., 1991. A number of general reactions such as oxidations and reductions are not shown in detail but can be done by methods understood by one skilled in the art. General transformations are well reviewed in "Comprehensive Organic Transformation" by Richard Larock, and the series "Compendium of Organic Synthetic Methods" (1989) published by Wiley-Interscience. In general, the starting materials were obtained from commercial sources unless otherwise indicated.

Preparation of Compounds

Compounds of Formulas I–III can be prepared by a reductive amination reaction between an amine and 4-(4-hydroxyphenyl)cyclohexanone (Scheme 1). Examples of synthetic procedures for the synthesis of amines and for reductive aminations are included. The amines thus generated can subsequently be converted to amides, carbamates, or more substituted amines. Examples of these processes are included.

Scheme 1

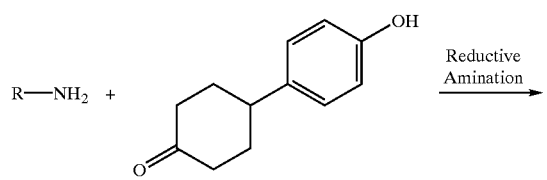

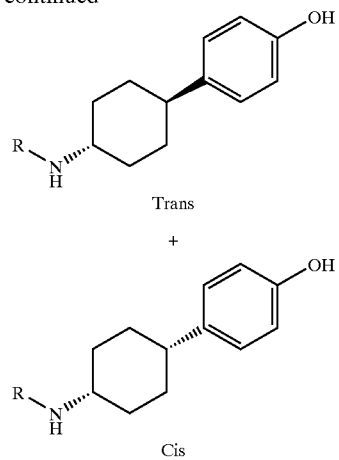

Compounds of Formulas I–III can also be prepared from cis- or trans-1-amino-4-(4-hydroxyphenyl)cyclohexane by alternative approaches including: reductive amination with aldehydes or ketones, amidation, and amidation followed by reduction (Scheme 2), and alkylation (Scheme 3). Examples of these processes are included. A method for the synthesis of trans-1-amino4-(4-hydroxyphenyl)cyclohexane is also included.

Scheme 2

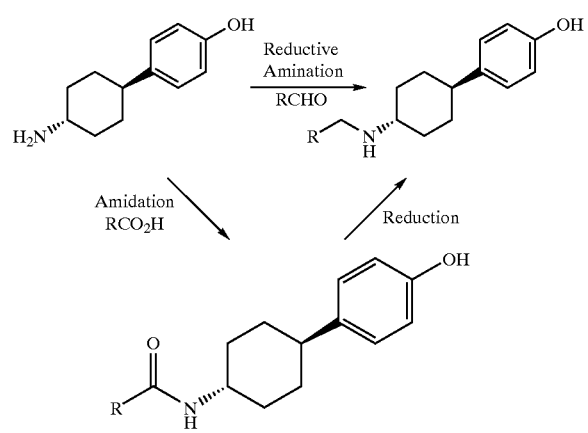

Scheme 3

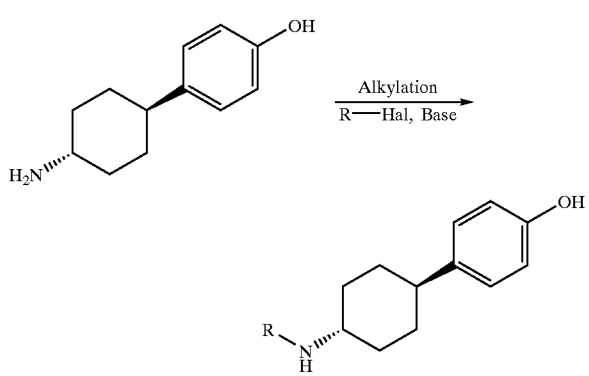

General Methods

HCl salts were prepared by treatment of a MeOH solution of the amine with excess HCl in Et₂O (1 M). The salts were isolated either by filtration if they precipitated directly from the ether solution, or by first removal of the solvent under reduced pressure, and then crystallization (Et$_2$O/MeOH).

Maleate salts were prepared by treatment of a MeOH solution of the amine with one equivalent of maleic acid in Et$_2$O. The salts were isolated either by filtration if they precipitated directly from the ether solution, or by first removal of the solvent under reduced pressure, and then crystallization (Et$_2$O/MeOH).

Purity was determined by reverse phase HPLC by the following methods:

Method A: column: YMC J'sphere C18, ODS-M80, 150×4.6 mm, 4μ;
  solvent A: 0.1% H$_3$PO$_4$ in H$_2$; solvent B: 0.1% H$_3$PO$_4$ in CH$_3$CN;
  gradient: 10–100% B over 15 min; flow: 1 mL·min$^{-1}$; detection: 210 nm.

Method B: column: YMC J'Sphere C18, ODS-M80, 150×4.6 mm, 4μ;
  solvent A: 0.1% H$_3$PO$_4$ in H$_2$O; solvent B: 0.1% H$_3$PO$_4$ in MeOH;
  gradient: 10–100% B over 15 min; flow: 1 mL·min$^{-1}$; detection: 210 nm.

Method C: column: Zorbax Eclipse XDB-C8,1 50×4.6 mm, 4μ;
  solvent A: 1% Et$_3$N in H$_2$O, H$_3$PO$_4$ (to give a pH of 3);
  solvent B: 1% Et$_3$N in CH$_3$CN, H$_3$PO$_4$ (to give a pH of 3);
  gradient: 10–100% B over 15 min; flow: 1 mL·min$^{-1}$; detection: 210 nm.

Method D: column: Zorbax Eclipse XDB-C8, 150×4.6 mm, 4μ;
  solvent A: 1% Et$_3$N in H$_2$O, H$_3$PO$_4$ (to give a pH of 3);
  solvent B: 1% Et$_3$N in MeOH, H$_3$PO$_4$ (to give a pH of 3);
  gradient: 10–100% B over 15 min; flow: 1 mL·min$^{-1}$; detection: 210 nm.

Known Compounds 3-(4-Pyridyl)propylamine (Mayer J. M., Testa B., *Helv. Chim. Acta,* 1982;65:1868–1884)

3-(3-Pyridyl)propylamine (CAS#: 41038-69-1; Mayer Supra., 1982; Hawes, Davis J., *Heterocycl. Chem.,* 1973;10:39)

3-(2-Pyridyl)propylamine (CAS#: 41038-69-1; Mayer, supra., 1982. Other references in Chem. Abs., see search)

4-Phenylbutylamine (Kuelz et al., *Chem. Ber.,* 1939:2161–2165 and commercially available from Aldrich Chemical Company)

5-Phenylpentylamine (Kotschetkow and Dudykina, *Zh. Obshch. Khim.,* 1958;28:2399–2403)

2-Methyl-2-phenoxypropionic acid (CAS# 943-45-3; Bischoff, *Chem. Ber.,* 1900;33:933)

Methanesulfonic acid 3-phenyl-prop-2-ynyl ester (CAS# 82490-61-7; Place P., Verniere C., Gore J., *Tetrahedron,* 1981;37:1359–1368)

3-(4-Methoxyphenyl)propionaldehyde (CAS# 20401-88-1; Walker E., *J. Chem. Soc.,* 1947:1571)

Preparation of trans-1-Amino4-(4-hydroxyphenyl) cyclohexane 5

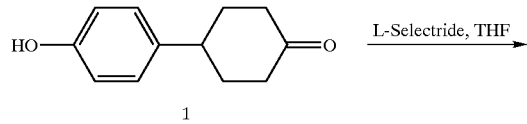

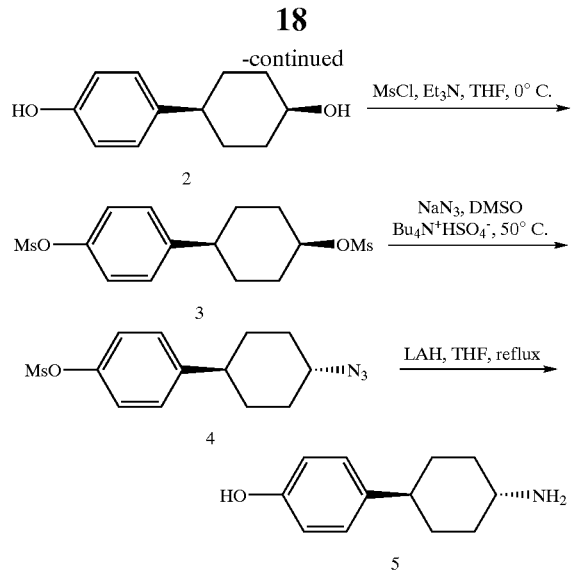

Step 1: To an ice-cold, stirred solution of 4-(4-hydroxyphenyl)-cyclohexanone 1 (5.0 g, 26 mmol) in THF (120 mL), under an N$_2$ atmosphere, was added L-selectride® (30 mL of a 1.0 M in THF, 30 mmol) dropwise over 15 minutes. The reaction mixture was allowed to warm to room temperature and then stirred overnight. The reaction mixture was diluted with MeOH (100 mL) and concentrated under reduced pressure. The residue was dissolved in MeOH, basic alumina added, and then concentrated under reduced pressure. The solid was loaded on to a silica column and the product eluted with 2:1 hexanes:EtOAc. Yield of alcohol 2 (4.4 g, 87%): $^1$H NMR (300 MHz, CD$_3$OD) δ 7.07 (d, J=8 Hz, 2H), 6.68 (d, J=8 Hz, 2H), 4.02 (m, 1H), 2.44 (tt, J=10, 2 Hz, 1H), 1.87 (m, 4H), 1.60 (m, 4H).

Step 2: To an ice-cold solution of alcohol 2 (0.5 g, 2.5 mmol) in THF (20 mL), under an N$_2$ atmosphere, was added Et$_3$N (1.0 mL, 7.2 mmol), followed by methanesulfonyl chloride (0.5 mL, 6.5 mmol). After 2 minutes, the reaction mixture was diluted with EtOAc and washed with 2N HCl, H$_2$O, saturated NaHCO$_3$, saturated NaCl, and dried (Na$_2$SO$_4$). Concentration under reduced pressure gave mesylate 3 (1.0 g, quant.), which was used without further purification: $^1$H NMR (300 MHz, CD$_3$OD) δ 7.28 (d, J=8 Hz, 2H), 7.20 (d, J=8 Hz, 2H), 5.05 (m, 1H), 3.13 and 3.04 (both s, 3H), 2.60 (tt, J=10, 2 Hz, 1H), 2.22 (m, 2H), 1.70 (m, 6H).

Step 3: To a solution of mesylate 3 (1.0 g, 2.5 mmol) in DMSO (5 mL) was added NaN$_3$ (0.5 g, 7.7 mmol). The reaction mixture was stirred at 50° C. overnight. After cooling, the reaction mixture was diluted with EtOAc, washed with H$_2$O and saturated NaCl and dried (Na$_2$SO$_4$). Concentration under reduced pressure, followed by purification by flash chromatography (eluent 6:1 to 4:1 hexanes:EtOAc) gave the azide 4 (0.6 g, 75%): $^1$H NMR (300 MHz, CDCl$_3$) δ 7.23 (m, 4H), 3.43 (tt, J=10, 2 Hz, 1H), 3.33 (s, 3H), 2.54 (tt, J=10, 2 Hz, 1H), 2.25 (m, 2H), 1.96 (m, 2H), 1.50 (m, 4H).

Step 4: To an ice-cold solution of azide 4 (6.85 g, 23.2 mmol) in THF (200 mL) was added LiAlH$_4$ (58 mL of a 1 M solution in Et$_2$O, 58 mmol). The mixture was heated under reflux overnight. After cooling to 0° C., a mixture of 2 M NaOH (1.6 mL) and H$_2$O (5.1 mL) was added dropwise. The solids were removed by filtration and then boiled with first EtOH and then MeOH to extract any bound product. All of the organic solutions were combined and concentrated under reduced pressure. The crude product was taken up in EtOH and dried over 3 Å molecular sieves. Basic alumina was added to the ethanolic solution, and the solvent was removed under reduced pressure. The solid was loaded onto a silica column (eluent 8:2 CHCl$_3$:MeOH, 7:3 CHCl$_3$:MeOH, 80:18:2 CHCl$_3$:MeOH:NH$_4$OH, and 70:27:3 CHCl$_3$:MeOH:NH$_4$OH). The product was further purified by triturating with CHCl$_3$. Yield of amine 5 (2.77 g, 63%): $^1$H NMR (300 MHz, CDCl$_3$) δ 7.02 (d, J=8 Hz, 2H), 6.68 (d, J=8 Hz, 2H), 2.48 and 2.28 (both tt, J=10, 2 Hz, 1H), 1.96 and 1.85 (both br d, J=10 Hz, 2H), 1.49 and 1.27 (both dddd, J=10, 10, 10, 2 Hz, 2H).

EXAMPLE 1

(a) cis-4-[4-(4-Phenylbutylamino)cyclohexyl]phenol
(b) trans-4-[4-(4-Phenylbutylamino)cyclohexyl]phenol
(Magid-Abdel A. F., Carson K. G., Harris B. D., Maryanoff C. A., Shah R. D., *J. Org. Chem.*, 1996;61:3849)

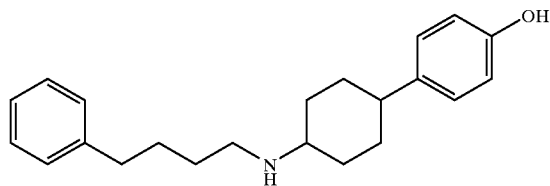

To a stirred solution of 4-phenylbutylamine (3.00 g, 20.10 mmol) and 4-(4-hydroxyphenyl)cyclohexanone 1 (3.82 g, 20.10 mmol) in 1,2-dichloroethane (70 mL) was added sodium triacetoxyborohydride (5.96 g, 28.14 mmol), followed by glacial acetic acid (1.20 g, 20.10 mnmol). The reaction mixture was stirred overnight. The solution was basified with 2N NaOH (20 mL) and extracted with EtOAc (500 mL). The organic layer was dried (Na$_2$SO$_4$) and concentrated under reduced pressure. Purification by flash chromatography (silica, 9:4:1 CH$_2$Cl$_2$:MeOH:NH$_4$OH) gave (a) the cis-isomer: cis-4-[4-(4-Phenylbutylamino) cyclohexyl]phenol (0.8 g, 12%): mp 128–131° C.; IR (KBr): 3293, 2934, 1611 cm$^{-1}$; $^1$H NMR (300 MHz, CD3OD) δ 7.29 (m, 5H), 7.08 (d, J=10 Hz, 2H), 6.72 (d, J=10 Hz, 2H), 2.82 (m, 1H), 2.65 (tt, J=7, 3 Hz, 2H), 2.65 (tt, J=7, 3 Hz, 2H), 2.51 (m, 1H), 1.89–1.54 (m, 12H); $^{13}$C NMR (75 MHz, DMSO-d$_6$) δ 155.2,142.3, 137.7, 128.2, 128.1, 127.9, 127.4, 125.5, 114.9, 51.2,46.6, 42.4,35.1, 30.0,29.4, 28.9, 28.1; CI-MS (methane) (m/z): 324 [M +H]$^+$; HPLC: method A, 6.21 minutes (98.4%); method B, 12.38 minutes (99.7%); Anal. Calcd for C$_{22}$H$_{29}$NO.0.33H$_2$O: C, 80.20; H, 9.08; N, 4.25. Found: C, 80.08; H, 8.96; N, 4.16.

Yield of the trans-isomer (b) trans-4-[4-(4-phenylbutylamino) cyclohexyl]-phenol (0.2 g, 4%): mp 161–171° C.; IR (KBr): 3275, 2924, 1611 cm$^{-1}$; $^1$H NMR (300 MHz, CD$_3$OD) δ 7.31–7.20 (m, 5H), 7.07 (d, J=9 Hz, 2H), 6.70 (d, J=9 Hz, 2H), 2.64 (tt, J=4, 4 Hz, 2H), 2.63 (tt, J=4, 4, 2H), 2.58 (tt, J=10, 2 Hz, 1H), 2.48 (tt, J=10, 2 Hz, 1H), 2.06 (br d, J=10 Hz, 2H), 1.85 (br d, J=10 Hz, 2H), 1.63 (quint, J=4 Hz, 2H), 1.58 (quint, J=4 Hz, 2H), 1.49(dddd, J=10, 10, 10, 2 Hz, 2H), 1.41 (dddd, J=10, 10, 10, 2 Hz, 2H); $^{13}$C NMR(75 MHz, CD$_3$OD) δ 156.6, 143.7, 139.3, 129.6, 129.5, 128.7, 126.9, 116.2, 57.9, 47.6, 44.7, 36.9, 34.5, 33.9,30.5, 30.2; CI-MS (methane) (m/z): 324 [M+H]$^+$; HPLC: method A, 6.17 minutes (96.0%); Anal. Calcd for C$_{22}$H$_{29}$NO: C, 81.69; H, 9.04; N, 4.33. Found: C, 81.41; H, 9.14; N, 4.30.

EXAMPLE 2

(a) cis-4-[4-(3-Phenylpropylamino)cyclohexyl]phenol
(b) trans-4-[4-(3-Phenylpropylamino)cyclohexyl]phenol

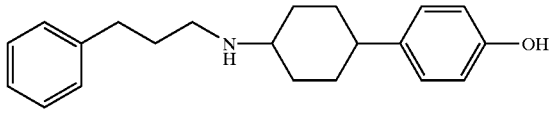

In a manner similar to Example 1, 3-phenylpropyl amine was allowed to react with 4-(4-hydroxyphenyl) cyclohexanone to give (1.4 g, 28%): (a) cis-4-[4-(3-phenylpropylamino)cyclohexyl]phenol: mp 115–123° C.; IR (KBr): 3303, 2929, 1611 cm$^{-1}$; $^1$H NMR (300 MHz, CD$_3$OD) δ 7.27–7.13 (m, 5H), 7.05 (d, J=9 Hz, 2H), 6.72 (d, J=9 Hz, 2H), 2.82 (m, 1H), 2.58–2.49 (m, 4H), 2.48 (m, 1H), 1.92–1.56 (m, 10H); $^{13}$C NMR (75 MHz, DMSO-d$_6$) δ 155.2, 142.3, 137.7, 128.2, 128.1, 127.3, 125.5, 114.8, 51.2, 46.3, 42.4, 33.0, 30.1, 28.1; API-MS (m/z): 310 [M+H]$^+$; HPLC: method A, 5.99 minutes (99.2%); Anal. Calcd for C$_{21}$H$_{27}$NO: C, 81.51; H, 8.79; N, 4.53. Found: C, 81.14; H, 8.88; N, 4.36.

And the trans-isomer (b) IUPAC: trans-4-[4-(3-phenylpropylamino) cyclohexyl]phenol (0.8 g, 15%): mp 154–157° C.; IR (KBr): 3268, 2925, 1612 cm$^{-1}$; $^1$H NMR (300 MHz, CD$_3$OD) δ 7.28–7.13 (m, 5H), 7.01 (d, J=9 Hz, 2H), 6.68 (d, J=9 Hz, 2H), 2.71 (tt, J=8, 8 Hz, 2H), 2.69 (tt, J=8, 8 Hz, 2H), 2.58 (tt, J=9, 2 Hz, 1H), 2.41 (tt, J=9, 2 Hz, 1H), 2.04 (br d, J=9 Hz, 2H), 1.89 (br d, J=9 Hz, 2H), 1.87 (quint, J=8 Hz, 2H), 1.48 (dddd, J=9, 9, 9, 2 Hz, 2H), 1.39 (dddd, J=9, 9, 9, 2 Hz, 2H); $^{13}$C NMR (75 MHz, DMSO-d$_6$) δ 155.3, 142.2, 137.1, 128.2, 127.9, 127.3, 125.6, 114.9, 56.2, 45.8, 42.7, 33.1, 32.9, 31.6; API-MS (m/z): 310 [M+H]$^+$; HPLC: method A, 5.89 minutes (99.7%); method B, 11.37 minutes (96.5%); Anal. Calcd for C$_{21}$H$_{27}$NO.0.33H$_2$O: C, 79.96; H, 8.84; N, 4.44. Found: C, 79.72; H, 8.93; N, 4.34.

EXAMPLE 3

(a) cis-4-(4-Phenethylaminocyclohexyl)phenol and
(b) trans-4-(4-Phenethylamiocyclohexyl)phenol.

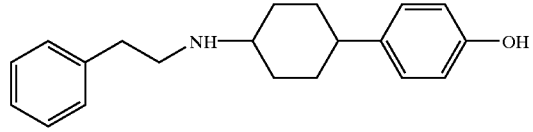

Yield of the cis-isomer (a) cis 4-(4-phenethylaminocyclohexyl)-phenol (3.0 g, 44%): mp 155–160° C.; IR (KBr): 3288, 2935, 1614 cm$^{-1}$; $^1$H NMR (300 MHz, DMSO-d$_6$) δ 9.11 (br s, 1H), 7.28–7.18 (m, 5H), 6.96 (d, J=8 Hz, 2H), 6.65 (d, J=8 Hz, 2H), 2.82 (m, 1H), 2.48 (m, 1H), 1.71–1.61 (m, 6H), 1.57–1.48 (m, 6H); $^{13}$C NMR (75 MHz, DMSO-d$_6$) δ 155.1, 141.2, 137.7, 128.5, 127.3, 125.7, 114.8, 50.7, 48.4, 42.3, 36.1, 30.0, 27.9; API-MS (m/z): 296 [M+H]$^+$; HPLC: method B, 11.02 minutes (97.2%); Anal. Calcd for C$_{20}$H$_{25}$NO.0.50H$_2$O: C, 78.91; H, 8.61; N, 4.60. Found: C, 79.20; H, 8.39; N, 4.44.

Yield of the trans-isomer (b) trans-4-(4-phenethylaminocyclohexyl) phenol (2.7 g, 41%): mp 147–149° C.; IR (KBr): 3276, 2916, 1611 cm$^{-1}$; $^1$H NMR (300 MHz, CD$_3$OD) δ 7.31–7.15 (m, 5H), 6.99 (d, J=9 Hz, 2H), 6.68 (d, J=9 Hz, 2H), 2.85 (tt, J=5, 5 Hz, 2H), 2.84 (tt, J=5, 5 Hz, 2H), 2.51 (tt, J=12, 2 Hz, 1H), 2.49 (tt, J=12, 2

Hz, 1H), 2.07 (br d, J=12 Hz, 2H), 1.86 (br d, J=12 Hz, 2H), 1.48 (dddd, J=12, 12, 12, 2 Hz, 2H), 1.24 (dddd, J=12, 12, 12, 2 Hz, 2H); $^{13}$C NMR (75 MHz, CD$_3$OD) δ 130.2, 130.1, 129.1, 127.8, 116.6, 58.2, 37.4, 34.9, 34.6; API-MS (m/z): 296 [M+H]$^+$; HPLC: method A, 6.40 minutes (94.4%); Anal. Calcd for C$_{20}$H$_{25}$NO: C, 81.31; H, 8.53; N, 4.74. Found: C, 81.24; H, 8.54; N, 4.52.

EXAMPLE 4

(a) cis-4-(4-Benzylaminocyclohexyl)phenol and
(b) trans-4-(4-Benzylaminocyclohexyl)phenol

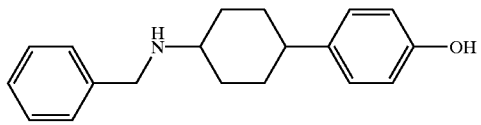

Yield of the cis-isomer (a) cis-4-(4-benzylamino-cyclohexyl)-phenol (1.3 g, 21%): mp 107–110° C.; IR (KBr): 3292, 2926, 1610 cm$^{-1}$; $^1$H NMR (300 MHz, DMSO-d$_6$) δ 9.09 (br s, 1H), 7.37–7.19 (m, 5H), 7.03 (d, J=9 Hz, 2H), 6.65 (d, J=9 Hz, 2H), 3.34 (s, 2H), 2.76 (m, 1H), 2.38 (m, 1H), 1.77–1.73 (m, 4H), 1.51–1.42 (m, 4H); $^{13}$C NMR (75 MHz, DMSO-d$_6$) δ 155.2, 141.6,137.8, 127.9, 127.9, 126.3, 114.9, 50.4, 50.1, 30.0, 28.1; API-MS (m/z): 282 [M+H]$^+$; HPLC: method A, 5.38 minutes (97.9%); method B, 5.30 minutes (97.9%); Anal. Calcd for C$_{19}$H$_{23}$NO.0.125H$_2$O: C, 80.45; H, 8.26; N, 4.94. Found: C, 80.52; H, 8.10; N, 4.84.

Yield of the trans-isomer (b) trans-4-(4-benzylaminocyclohexyl)phenol (0.8 g, 12%): mp 168–172° C.; IR (KBr): 3279, 2918, 1613 cm$^{-1}$; $^1$H NMR (300 MHz, CD$_3$OD) δ 7.36–7.24 (m, 5H), 7.01 (d, J=8 Hz, 2H), 6.68 (d, J=8 Hz, 2H), 3.80 (s, 2H), 2.48 (tt, J=13, 3 Hz, 1H), 2.43 (tt, J=13, 3 Hz, 1H), 2.10 (br d, J=13 Hz, 2H), 1.84 (br d, J=13 Hz, 2H), 1.46 (dddd, J=13, 13, 13, 3 Hz, 2H), 1.44 (dddd, J=13, 13, 13, 3 Hz, 2H); $^{13}$C NMR (75 MHz, DMSO-d$_6$) δ 155.3, 137.2, 127.9, 127.8, 127.3, 126.2, 114.9, 55.4, 50.0, 42.7, 33.3, 32.9; API-MS (m/z): 282 [M+H]$^+$; HPLC: method A, 5.13 minutes (97.7%); method B, 5.07 minutes (90.8%); Anal. Calcd for C$_{19}$H$_{23}$NO.0.125H$_2$O: C, 80.45; H, 8.26; N, 4.94. Found: C, 80.24; H, 8.27; N, 4.92.

EXAMPLE 5

(a) cis-4-{4-[2-(4-Fluorophenyl)ethylamino]cyclohexyl}phenol
(b) trans-4-{4-[2-(4-Fluorophenyl)ethylamino]cyclohexyl}phenol

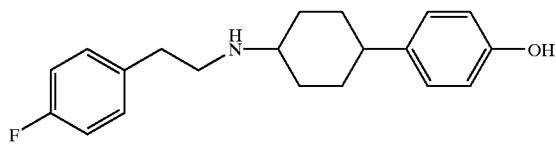

The cis-isomer (a) cis-4-{4-[2-(4-fluoro-phenyl)-ethylamino]-cyclohexyl}-phenol was isolated as the HCl salt (1.2 g, 20%): mp 234–237° C.; IR (KBr): 3252, 2941, 1612 cm$^{-1}$; $^1$H NMR (300 MHz, DMSO-d$_6$) δ 9.06 (br s, 1H), 7.34 (dd, J=8, 6, Hz, 2H), 7.19 (dd, J=8, 6 Hz, 2H), 7.16 (d, J=8 Hz, 2H), 6.69 (d, J=8 Hz, 2H), 3.11 (m, 4H), 3.08 (m, 1H), 2.51 (m, 1H), 2.02 (m, 4H), 1.72 (m, 2H), 1.59 (m, 2H); CI-MS (methane) (m/z): 314 [M+H]$^+$; HPLC: method A, 5.47 minutes (99.3%); Anal. Calcd for C$_{20}$H$_{24}$FNO.HCl: C, 68.66; H, 7.20; N, 4.00. Found: C, 68.55; H, 7.41; N, 4.36.

The trans-isomer (b) trans-4-{4-[2-(4-fluorophenyl)ethylamino]-cyclohexyl}phenol was isolated as the HCl salt (0.2 g, 5%): mp 239–242° C.; IR (KBr): 3252, 2941, 1612cm$^{-1}$; $^1$H NMR (300 MHz, DMSO-d$_6$) δ 9.16 (s, 1H), 7.34 (dd, J=7, 6, Hz, 2H), 7.17 (dd, J=7, 6 Hz, 2H), 7.00 (d, J=9 Hz, 2H), 6.69 (d, J=9 Hz, 2H), 3.16 (m, 4H), 3.13 (m, 1H), 2,98 (m, 2H), 2.48 (m, 1H), 2.15 (br d, J=8 Hz, 2H), 1.82 (br d, J=8 Hz, 2H), 1.44 (dddd, J=8, 8, 8, 2, 4H); API-MS (m/z): 324 [M+H]$^+$; HRMS-API (m/z): [M+H]$^+$ Calcd for C$_{20}$H$_{24}$FNO, 324.2327. found: 324.2324. HPLC: method A, 7.61 minutes (96.5%); method B, 13.60 minutes (99.9%); Anal. Calcd for C$_{20}$H$_{24}$FNO.HCl.H$_2$O: C, 65.30; H, 7.40; N, 3.81. Found: C, 65.59; H, 7.35; N, 3.75.

EXAMPLE 6

(a) trans-4-[4-(1-Methyl-3-phenylpropylamino)cyclohexyl]phenol
(b): cis-4-[4-(1-Methyl-3-phenylpropylamino)cyclohexyl]phenol
(c) trans-4-[4-((R)-1-Methyl-3-phenylpropylamino)cyclohexyl]phenol
(d) trans-4-[4-((S)-1-Methyl-3-phenylpropylamino)cyclohexyl]phenol

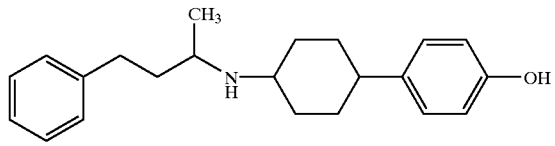

The cis-isomer (a) cis-4-[4-(1-methyl-3-phenylpropylamino) cyclohexyl]phenol was isolated as the HCl salt (1.9 g, 40%): mp 204–214° C.; IR (KBr): 3250, 2942, 1613 cm$^{-1}$; $^1$H NMR (300 MHz, DMSO-d$_6$) δ 9.17 (br s, 1H) 7.31–7.20 (m, 5H), 7.15 (d, J=9 Hz, 2H), 6.69 (d, J=9 Hz, 2H), 3.32 (m, 1H), 2.74 (m, 1H), 2.57 (m, 1H), 2.19–1.93 (m, 2H), 1.74–1.52 (m, 9H), 1.33 (d, J=7 Hz, 3H); CI-MS (methane) (m/z): 324 [M+H]$^+$; HPLC: method A, 6.14 minutes (98.1%); method B, 6.16 minutes (97.9%); Anal. Calcd for C$_{22}$H$_{29}$NO.HCl: C, 73.41; H, 8.40; N, 3.89. Found: C, 73.17; H, 8.45; N, 3.79.

The trans-isomer (b) trans-4-[4-(1-methyl-3-phenylpropylamino)-cyclohexyl]phenol was isolated as the HCl salt (1.2 g, 21%): mp 169–176° C.; IR (KBr): 3260, 2924, 1612 cm$^{-1}$; $^1$H NMR (300 MHz, DMSO-d$_6$) δ 9.08 (s, 1H), 7.28–7.12 (m, 5H), 6.97 (d, J=8 Hz, 2H), 6.64 (d, J=8 Hz, 2H), 2.73 (tt, J=12, 3 Hz, 1H), 2.64 (t, J=7 Hz, 2H), 2.54 (m, 1H), 2.45 (tt, J=12, 3 Hz, 1H), 1.93–1.04 (m, 10H), 1.01 (d, J=7 Hz, 3H); CI-MS (methane) (m/z): 324 [M+H]$^+$; HPLC: method A, 5.64 minutes (99.8%); method B, 6.14 minutes (98.1%); Anal. Calcd for C$_{22}$H$_{29}$NO.0.125H$_2$O: C, 81.12; H, 9.05; N, 4.30. Found: C, 81.09; H, 9.04; N, 4.19.

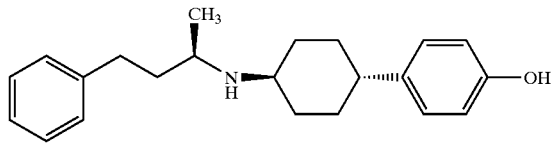

(c) trans-4-[4-((R)-1-Methyl-3-phenylpropylamino) cyclohexyl] phenol was isolated as the free base (0.3 g, 6%): mp 152–160° C.; IR (KBr): 3265, 2926, 1616 cm$^{-1}$; $^1$H NMR (300 MHz, DMSO-d$_6$) δ 9.08 (s, 1H), 7.28–7.12 (m, 5H), 6.97 (d, J=8 Hz, 2H), 6.64 (d, J=8 Hz, 2H), 2.73 (tt, J=12, 3 Hz, 1H), 2.64 (t, J=7 Hz, 2H), 2.54 (m, 1H), 2.45 (tt, J=12, 3 Hz, 1H), 1.93–1.04 (m, 10H), 1.01 (d, J=7 Hz, 3H); CI-MS (methane) (m/z): 324 [M+H]⁺; HPLC: method A, 7.90 minutes (99.5%); method B, 14.46 minutes (97.6%); Anal. Calcd for C$_{22}$H$_{29}$NO: C, 81.69; H, 9.04; N, 4.33. Found: C, 81.65; H, 9.25; N, 4.15.

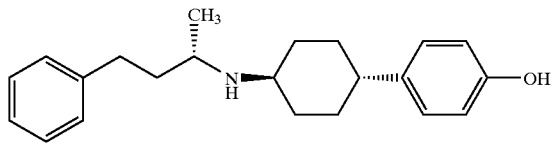

(d) trans-4-[4-((S)-1-Methyl-3-phenylpropylamino) cyclohexyl]phenol was isolated as the free base (0.35 g, 7%): mp 165–170° C.; IR (KBr): 3268, 2926, 1612 cm$^{-1}$; $^1$H NMR (300 MHz, DMSO-d$_6$) δ 9.08 (s, 1H), 7.28–7.12 (m, 5H), 6.97 (d, J=8 Hz, 2H), 6.64 (d, J=8 Hz, 2H), 2.73 (tt, J=12, 3 Hz, 1H), 2.64 (t, J=7 Hz, 2H), 2.54 (m, 1H), 2.45 (tt, J=12, 3 Hz, 1H), 1.93–1.04 (m, 10H), 1.01 (d, J=7 Hz, 3H); CI-MS (methane) (m/z): 324 [M+H]⁺; HRMS-API (m/z): [M+H]⁺ Calcd for C$_{22}$H$_{29}$NO, 324.2327. found: 324.2324. HPLC: method A, 7.87 minutes (97.9%); method B, 11.22 minutes (96.9%); Anal. Calcd for C$_{22}$H$_{29}$NO: C, 81.69; H, 9.04; N, 4.33. Found: C, 81.35; H, 9.01; N, 4.30.

EXAMPLE 7

(a) cis-4-{4-[(Pyridin-3-ylmethyl)amino]cyclohexyl}phenol
(b) trans-4-{4-[(Pyridin-3-ylmethyl)amino] cyclohexyl}phenol

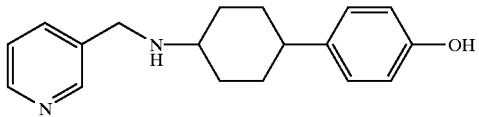

The cis-isomer (a) cis-4-{4-[(pyridin-3-ylmethyl)amino] cyclohexyl}-phenol was isolated as the bis-HCl salt (1.85 g, 36%): mp 151–162° C.; IR (KBr): 2936, 1612, 1516 cm$^{-1}$; $^1$H NMR (300 MHz, CD$_3$OD) δ 9.21 (s, 1H), 8.95 (d, J=8, 6 Hz, 1H), 8.88 (d, J=8 Hz, 1H), 8.18 (dd, J=8, 6Hz, 1H), 7.19 (d, J=8 Hz, 2H), 6.72 (d, J=8 Hz, 2H), 4.59 (s, 2H), 3.61–3.55 (m, 1H), 2.79–2.59 (m, 1H), 2.15–1.95 (m, 6H), 1.90–1.78 (m, 2H); $^{13}$C NMR (75 MHz, CD$_3$OD) δ 156.8, 149.9, 145.1, 143.8, 137.2, 133.6, 129.2, 128.8, 116.3, 57.95, 46.7, 41.3, 29.1, 27.6; CI-MS (methane) (m/z): 283 [M+H]⁺; HPLC: method C, 10.76 minutes (99.6%); Anal. Calcd for C$_{18}$H$_{22}$N$_2$O.2HCl: C, 60.85; H, 6.81; N, 7.88. Found: C, 60.42; H, 6.94; N, 7.69.

The trans-isomer (b) trans-4-{4-[(pyridin-3-ylmethyl) amino]cyclohexyl}-phenol was isolated as the bis-HCl salt (0.18 g, 4%): mp 309–312° C.; IR (KBr): 3169, 2940, 1613, 1516 cm$^{-1}$; $^1$H NMR (300 MHz, CD$_3$OD) δ 9.08 (s, 1H), 8.93 (d, J=6 Hz, 1H), 8.70 (d, J=8 Hz, 1H), 8.11 (dd, J=8, 6 Hz, 1H), 7.05 (d, J=8 Hz, 2H), 6.71 (d, J=8 Hz, 2H), 4.55 (s, 2H), 3.36 (tt, J =10, 2 Hz, 1H), 2.52 (tt, J=10, 2 Hz, 1H), 2.36 (br d, J=10 Hz, 2H), 2.02 (br d, J=10 Hz, 2H), 1.60 (dddd, 10, 10, 10, 2 Hz, 4H); CI-MS (methane) (m/z): 283 [M+H]⁺; HPLC: method C, 6.26 minutes (99.9%); Anal. Calcd for C$_{18}$H$_{22}$N$_2$O.2HCl: C, 60.85; H, 6.81; N, 7.88. Found: C, 60.92; H, 6.85; N, 7.81.

EXAMPLE 8

(a) cis-4-{4-[2-(4-Methoxyphenyl)ethylamino] cyclohexyl}phenol
(b) trans-4-{4-[2-(4-Methoxyphenyl)ethylamino] cyclohexyl}phenol

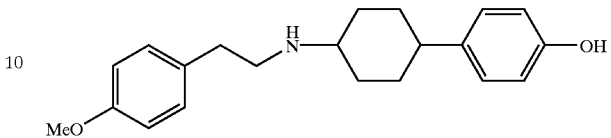

The cis-isomer (a) cis-4-{4-[2-(4-methoxyphenyl) ethylamino]-cyclohexyl}phenol was isolated as the free base (1.5 g, 34%): mp 145–148° C.; IR (KBr): 3296, 2930, 1612 cm$^{-1}$; $^1$H NMR (300 MHz, DMSO-d$_6$) δ 9.06 (br s, 1H), 7.14 (d, J=9 Hz, 2H), 6.93 (d, J=9 Hz, 2H), 6.84 (d, J=9 Hz, 2H), 6.63 (d, J=9 Hz, 2H), 3.43 (s, 3H), 2.78 (m, 1H), 2.66 (m, 4H), 2.33 (m, 1H), 1.72–1.35 (m, 8H); CI-MS (methane) (m/z): 326 [M+H]⁺; HRMS-API (m/z): [M+H]⁺ Calcd for C$_{21}$H$_{27}$NO$_2$, 326.2120. found: 326.2118. HPLC: method A, 5.81 minutes (99.7%); method B, 11.12 minutes (99.2%); Anal. Calcd for C$_{21}$H$_{27}$NO$_2$.0.25H$_2$O: C, 76.44; H, 8.40; N, 4.25. Found: C, 76.38; H, 8.33; N, 4.22.

The trans-isomer (b) IUPAC: trans-4-{4-[2-(4-Methoxyphenyl) ethylamino]cyclohexyl}phenol was isolated as the free base (1.0 g, 18%): mp 146–152° C.; IR (KBr): 3286, 2926, 1612 cm$^{-1}$; $^1$H NMR (300 MHz, DMSO-d$_6$) δ 9.09 (s, 1H), 7.14 (d, J=9 Hz, 2H), 6.99 (d, J=9 Hz, 2H), 6.84 (d, J=9 Hz, 2H), 6.65 (d, J=9 Hz, 2H), 3.45 (s, 3H), 2.61 (tt, J=7, 7 Hz, 2H), 2.60 (tt, J=7, 7 Hz, 2H), 2.42 (tt,J=9, 2 Hz, 1H), 2.42 (tt, J=9, 2 Hz, 1H), 1.93 (br d, J=9 Hz, 2H), 1.74 (br d, J=9 Hz, 2H), 1.35 (dddd, J=9, 9, 9, 2 Hz, 2H), 1.11 (dddd, J=9, 9, 9, 2 Hz, 2H); CI-MS (methane) (m/z): 326 [M+H]⁺; HRMS-API (m/z): [M+H]⁺ Calcd for C$_{21}$H$_{27}$NO$_2$, 326.2120. found: 326.2129. HPLC: method A, 5.69 minutes (97.9%); method B, 11.15 minutes (97.8%); Anal. Calcd for C$_{21}$H$_{27}$NO$_2$.0.25H$_2$O: C, 76.44; H, 8.40; N, 4.25. Found: C, 76.38; H, 8.23; N, 4.24.

EXAMPLE 9

4-[4-(5-Phenylpentylamino)cyclohexyl]phenol

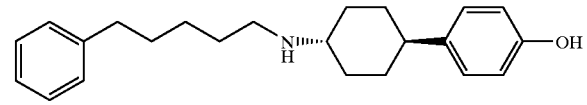

4-[4-(5-Phenylpentylamino)cyclohexyl]phenol was isolated as the HCl salt (0.5 g, 7%): mp 252–260° C.; IR (KBr): 3243, 2937, 1613 cm$^{-1}$; $^1$H NMR (300 MHz, DMSO-d$_6$) δ 9.16 (s, 1H), 7.31–7.14 (m, 5H), 6.97 (d, J=9 Hz, 2H), 6.66 (d, J=9 Hz, 2H), 3.01 (m, 1H), 2.96 (m, 2H), 2.67 (t, J=7 Hz, 2H), 2.39 (m, 2H), 2.17 (m, 2H), 1.83 (m, 2H), 1.73–1.38 (m, 10H); CI-MS (methane) (m/z): 338 [M+H]⁺; HRMS-API (m/z): [M+H]⁺ Calcd for C$_{23}$H$_{31}$NO, 338.2484. found: 338.2480. HPLC: method A, 6.61 minutes (93.7%); method B, 12.25 minutes (98.7%); Anal. Calcd for C$_{23}$H$_{31}$NO.HCl.0.25H$_2$O: C, 72.99; H, 8.66; N, 3.70. Found: C, 72.75; H, 8.62; N, 3.61.

EXAMPLE 10

(a) cis-4-[4-((R)-1-Hydroxymethyl-2-phenylethylamino)cyclohexyl]phenol
(b) trans-4-[4-((R)-1-Hydroxymethyl-2-phenylethylamino)cyclohexyl]phenol

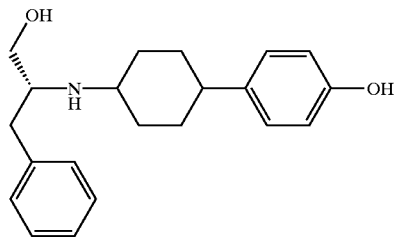

The cis-isomer (a) cis-4-[4-((R)-1-hydroxymethyl-2-phenylethylamino)-cyclohexyl]phenol was isolated as the HCl salt (0.44 g, 10%): mp 194–198° C.; IR (KBr): 3274, 1613, 1516 cm$^{-1}$; $^1$H NMR (300 MHz, CD$_3$OD) δ 7.40–7.27 (m, 5H), 7.14 (d, J=9 Hz, 2H), 6.73 (d, J=9 Hz, 2H), 3.78–3.69 (m, 1H), 3.58–3.49 (m, 3H), 3.13–2.97 (m, 2H), 2.82–2.75 (m, 1H), 2.11–1.76 (m, 8H); $^{13}$C NMR(75 MHz, DMSO-d$_6$) δ 155.4, 137.1, 135.7, 129.3, 128.5, 128.0, 126.7, 115.0, 58.9, 57.5, 51.9, 33.5, 27.4, 26.0, 26.0; CI-MS (methane) (m/z): 326 [M+H]$^+$; HRMS-API (m/z): [M+H]$^+$ Calcd for C$_{21}$H$_{27}$NO$_2$, 326.2120. found: 326.2121. HPLC: method A, 5.53 minutes (99.2%); method B, 10.36 minutes (99.7%); Anal. Calcd for C$_{21}$H$_{27}$NO$_2$.HCl.0.25H$_2$O: C, 68.84; H, 7.84; N, 3.82. Found: C, 69.07; H, 7.85; N, 3.73.

The trans-isomer (b) trans-4-[4-((R)-1-hydroxymethyl-2-phenylethylamino)cyclohexyl]phenol was isolated as the HCl salt (0.28 g, 7%): mp 191–198° C.; IR (KBr): 3316, 2950, 1615, 1515 cm$^{-1}$; $^1$H NMR (300 MHz, CD$_3$OD) δ 7.41–7.26 (m, 5H), 7.03 (d, J=9 Hz, 2H), 6.70 (d, J=9 Hz, 2H), 3.73 (br d, J=12 Hz, 1H), 3.60–3.50 (m, 2H), 3.31–3.23 (m, 1H), 3.01–2.98 (m, 2H), 2.55–2.45 (m, 1H), 2.30–2.20 (m, 2H), 2.01–1.93 (m, 2H), 1.68–1.48 (m, 4H); $^{13}$C NMR (75 MHz, DMSO-d$_6$) δ 129.2, 128.4, 127.2, 126.6, 115.0, 57.6, 57.1, 53.5, 41.5, 33.5, 31.9, 28.5, 28.3; CI-MS (methane) (m/z): 326 [M+H]$^+$; HRMS-API (m/z): [M+H]$^+$ Calcd for C$_{21}$H$_{27}$NO$_2$, 326.2120. found: 326.2122. HPLC: method A, 5.43 minutes (98.2%); method B, 10.03 minutes (98.3%); Anal. Calcd for C$_{21}$H$_{27}$NO$_2$.HCl.0.25H$_2$O: C, 68.84; H, 7.84; N, 3.82. Found: C, 68.61; H, 8.07; N, 3.66.

EXAMPLE 11

(a) cis-4-[4-(2-Phenoxyethylamino)cyclohexyl]phenol
(b) trans-4-[4-(2-Phenoxyethylamino)cyclohexyl]phenol

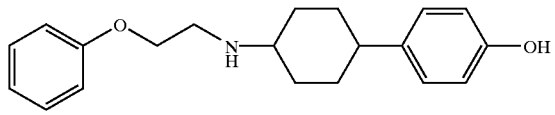

The cis-isomer (a) cis-4-[4-(2-phenoxyethylamino)cyclohexyl] phenol was isolated as the free base (1.1 g, 31%): mp 165–172° C.; IR (KBr): 3261, 2933, 1601 cm$^{-1}$; $^1$H NMR (300 MHz, DMSO-d$_6$) δ 9.07 (brs, 1H), 7.39 (t, J=7, 7 Hz, 3H), 7.03 (t, J=7, 7 Hz, 2H), 6.98 (d, J=9 Hz, 2H), 6.68 (d, J=9 Hz, 2H), 4.05 (t, J=6, 6 Hz, 2H), 2.87 (m, 2H), 2.85 (m, 1H), 2.40 (m, 1H), 1.79–1.43 (m, 8H); CI-MS (methane) (m/z): 312 [M+H]$^+$; HRMS-API (m/z): [M+H]$^+$ Calcd for C$_{20}$H$_{25}$NO$_2$, 312.1963. found: 312.1967. HPLC: method A, 5.51 minutes (98.7%); method B, 9.95 minutes (97.3%); Anal. Calcd for C$_{20}$H$_{25}$NO$_2$.0.125H$_2$O: C, 76.58; H, 8.11; N, 4.42. Found: C, 76.62; H, 8.04; N, 4.39.

The trans-isomer (b) trans-4-[4-(2-phenoxyethylamino)cyclohexyl]-phenol was isolated as the free base (0.5 g, 10%): mp 190–196° C.; IR (KBr): 3245, 2926, 1602 cm$^{-1}$; $^1$H NMR (300 MHz, DMSO-d$_6$) δ 9.09 (s, 1H), 7.29 (dd, J=9, 9 Hz, 2H), 6.99 (d, J=9 Hz, 2H), 6.93 (d, J=9 Hz, 2H), 6.64 (d, J=9 Hz, 2H), 4.00 (t, J=5 Hz, 2H), 2.92 (t, J=5 Hz, 2H), 2.51 (tt, J=11, 2 Hz, 2H), 2.49 (tt, J=11, 2 Hz, 2H), 2.01 (br d, J=11 Hz, 2H), 1.74 (br d, J=11 Hz, 2H), 1.42 (dddd, J=11, 11, 11, 2 Hz, 2H), 1.14 (dddd, J=11, 11, 11, 2 Hz, 2H); CI-MS (methane) (m/z): 312 [M+H]$^+$; HRMS-API (m/z): [M+H]$^+$ Calcd for C$_{20}$H$_{25}$NO$_2$, 312.1963. found: 312.1953. HPLC: method A, 5.36 minutes (96.7%); method B, 10.02 minutes (97.3%); Anal. Calcd for C$_{20}$H$_{25}$NO$_2$.0.33H$_2$O: C, 79.96; H, 8.84; N, 4.44. Found: C, 79.82; H, 8.84; N, 4.14.

EXAMPLE 12

(a) cis-4-[4-(3-Pyridin-4-ylpropylamino)cyclohexyl]phenol
(b) trans-4-[4-(3-Pyridin-4-ylpropylamino)cyclohexyl]phenol

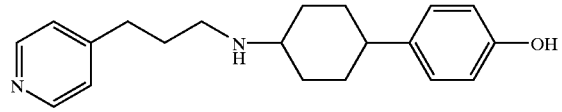

The cis-isomer (a) cis-4-[4-(3-pyridin-4-ylpropylamino)cyclohexyl]-phenol was isolated as the bis-HCl salt (0.56 g, 11%): mp 261–268° C.; IR (K.Br): 3158, 2942, 1636, 1610, 1515 cm$^{-1}$; $^1$H NMR (300 MHz, CD$_3$OD) δ 8.78 (d, J=6 Hz, 2H), 8.04 (d, J=6 Hz, 2H), 7.15 (d, J=8 Hz, 2H), 6.72 (d, J=8 Hz, 2H), 3.47–3.38 (m, 1H), 3.19–3.04 (m, 4H), 2.77–2.64 (m, 2H), 2.29–2.14 (m, 2H), 2.09–1.71 (m, 7H); $^{13}$C NMR (75 MHz, CD$_3$OD) δ 164.5, 156.8, 142.6, 137.5, 129.3, 128.8, 116.4, 56.7, 46.3, 41.6, 33.9, 29.0, 27.7, 27.2; CI-MS (methane) (m/z): 311 [M+H]$^+$; HRMS-API (m/z): [M+H]$^+$ Calcd for C$_{20}$H$_{26}$N$_2$O, 311.2123. found: 311.2115. HPLC: method C, 5.66 minutes (97.8%); method D, 13.03 minutes (97.8%); Anal. Calcd for C$_{20}$H$_{26}$N$_2$O.2HCl.0.25H$_2$O: C, 61.93; H, 7.41; N, 7.22. Found: C, 61.74; H, 7.51; N, 7.06.

The trans-isomer (b) trans-4-[4-(3-pyridin-4-ylpropylamino) cyclohexyl]-phenol was isolated as the maleate salt (0.20 g, 4%): mp 192–196° C.; IR (KBr): 2937, 1516 cm$^{-1}$; $^1$H NMR (300 MHz, CD$_3$OD) δ 8.46 (d, J=6, Hz, 2H), 7.34 (d, J=6, Hz, 2H), 7.04 (d, J=8 Hz, 2H), 6.70 (d, J=8 Hz, 2H), 6.25 (s, 2H), 3.17 (tt, J=10, 2 Hz, 1H), 3.09 (t, J=8 Hz, 2H), 2.88 (t, J=8 Hz, 2H), 2.47 (tt, J=10, 2 Hz, 1H), 2.47 (d, J=8 Hz, 2H), 2.10–1.91 (m, 4H), 1.55 (dddd, 10, 10, 10, 2 Hz, 4H); CI-MS (methane) (m/z): 311 [M+H]$^+$; HRMS-API (m/z): [M+H]$^+$ Calcd for C$_{20}$H$_{26}$N$_2$O, 311.2123. found: 311.2110; HPLC [free base]: method C, 6.68 minutes (99.1%); Anal. Calcd for C$_{20}$H$_{26}$N$_2$O.C$_4$H$_4$O$_4$: C, 67.59; H, 7.09; N, 6.57. Found: C, 67.21; H, 7.26; N, 6.33.

EXAMPLE 13 trans-4-[4-((S)-1-Methyl-2-phenylethylamino)cyclohexyl]phenol

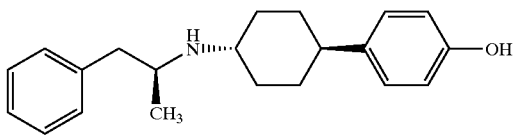

The trans-isomer trans-4-[4-((S)-1-methyl-2-phenylethylamino) cyclohexyl]phenol was isolated as the free base (0.7 g, 12%): mp 183–187° C.; IR (KBr): 3287, 2922, 1612 cm$^{-1}$; $^1$H NMR (300 MHz, DMSO-d$_6$) δ 7.31–7.15 (m, 5H), 6.96 (d, J=8 Hz, 2H), 6.68 (d, J=8 Hz, 2H), 2.82–2.64 (m, 3H), 2.49 (tt, J=12, 3 Hz, 1H), 2.48 (tt, J=12, 3 Hz, 1H), 1.94 (br d, J=12 Hz, 2H), 1.39 (br d, J=12 Hz, 2H), 1.38 (dddd, J=12, 12, 12, 3 Hz, 2H), 1.19 (d, J=13 Hz, 3H), 1.09 (dddd, J=12, 12, 12, 3 Hz, 2H); CI-MS (methane) (m/z): 310 [M+H]$^+$; HRMS-API (m/z): [M+H]$^+$ Calcd for C$_{21}$H$_{27}$NO, 310.2171. found: 310.2166; HPLC: method A, 5.47 minutes (99.8%); method B, 10.49 minutes (99.7%); Anal. Calcd for C$_{21}$H$_{27}$NO.0.33H$_2$O: C, 79.96; H, 8.84; N, 4.44. Found: C, 79.82; H, 8.84; N, 4.14.

EXAMPLE 14

(a) cis-4-[4-(3-Pyridin-3-ylpropylamino)cyclohexyl]phenol
(b) trans-4-[4-(3-Pyridin-3-ylpropylamino)cyclohexyl]phenol

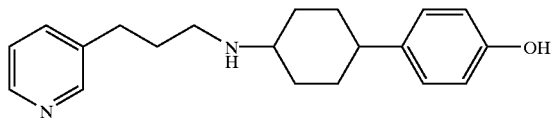

The cis-isomer(a) cis-4-[4-(3-pyridin-3-ylpropylamino) cyclohexyl]phenol was isolated as the maleate salt (2.05 g, 32%): mp 158–162° C.; IR (KBr): 2943, 1578, 1516 cm$^{-1}$; $^1$H NMR (300 MHz, CD$_3$OD) δ 8.45 (s, 1H), 8.41 (d, J=5 Hz, 1H), 7.74 (d, J=8 Hz, 1H), 7.41 (dd, J=8, 5 Hz, 1H), 7.11 (d, J=8 Hz, 2H), 6.72 (d, J=8 Hz, 2H), 6.25 (s, 2H), 3.41–3.55 (m, 1H), 3.09 (t, J=8 Hz, 2H), 2.78 (t, J=8 Hz, 2H), 2.75–2.68 (m, 1H), 2.03 (d, J=8 Hz, 2H), 1.95–1.77 (m, 8H); $^{13}$C NMR (75 MHz, DMSO-d$_6$) δ 167.1, 155.4, 149.4, 147.4, 136.12, 135.8, 135.6, 127.7, 123.5, 114.9, 53.5, 44.3, 29.0, 27.1, 26.9, 25.8; CI-MS (methane) (m/z): 311 [M+H]$^+$; HRMS-API (m/z): [M+H]$^+$ Calcd for C$_{20}$H$_{26}$N$_2$O, 311.2123. found: 311.2111; HPLC [free base]: method C, 6.55 minutes (99.7%), method D; 8.28 minutes (98.6%); Anal. Calcd for C$_{20}$H$_{26}$N$_2$O.C$_4$H$_4$O$_4$.0.25H$_2$O: C, 66.88; H, 7.13; N, 6.50. Found: C, 66.90; H, 7.04; N, 6.32.

The trans-isomer (b) trans-4-[4-(3-pyridin-3-ylpropylamino)cyclohexyl]phenol was isolated as the maleate salt (0.18 g, 3%): mp 175–180° C.; IR (KBr): 2938, 1617, 1576, 1516 cm$^{-1}$; $^1$H NMR (300 MHz, CD$_3$OD) δ 8.45 (s, 1H), 8.42 (d, J=5 Hz, 1H), 7.76 (d, J=8 Hz, 1H), 7.41 (dd, J=8, 5 Hz, 1H), 7.03 (d, J=8 Hz, 2H), 6.70 (d, J=8 Hz, 2H), 6.24 (s, 2H), 3.21–3.05 (m, 1H), 3.09 (t, J=8 Hz, 2H), 2.80 (t, J=8 Hz, 2H), 2.55–2.44 (m, 1H), 2.20 (d, J=8 Hz, 2H), 2.10–1.91 (m, 4H), 1.67–1.45 (m, 4H); CI-MS (methane) (m/z): 311 [M+H]$^+$; HRMS-API (m/z): [M+H]$^+$ Calcd for C$_{20}$H$_{26}$N$_2$O, 311.2123. found: 311.2128; HPLC [free base]: method C, 7.78 minutes (99.3%); method D, 7.24 minutes (99.3%); Anal. Calcd for C$_{20}$H$_{26}$N$_2$O.C$_4$H$_4$O$_4$.0.25H$_2$O: C, 66.88; H, 7.13; N, 6.50. Found: C, 66.96; H, 7.10; N, 6.30.

EXAMPLE 15

(a) cis-4-[4-(3-Pyridin-2-ylpropylamino)cyclohexyl]phenol
(b) trans-4'-(3-Pyridin-2-ylpropylamino)cyclohexylphenol

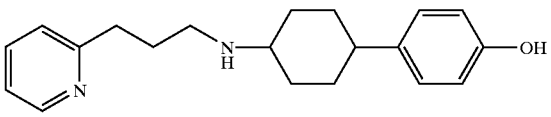

The cis-isomer (a) cis-4-[4-(3-pyridin-2-ylpropylamino) cyclohexyl]-phenol was isolated as the maleate salt (1.1 g, 14%): mp 137–140° C.; IR (KBr): 2948, 1581, 1516 cm$^{-1}$; $^1$H NMR (300 MHz, CD$_3$OD) δ 8.47 (d, J=5 Hz, 1H), 7.80 (t, J=6 Hz, 1H), 7.36 (d, J=8 Hz, 1H), 7.12 (d, J=8Hz, 2H), 6.72 (d, J=8 Hz, 2H), 6.25 (s, 2H), 3.42–3.36 (m, 1H), 3.13 (t, J=8 Hz, 2H), 2.95 (t, J=8 Hz, 2H), 2.76–2.68 (m, 1H), 2.18–2.07 (m, 2H), 2.00–1.75 (m, 8H); $^{13}$C NMR (75 MHz, DMSO-d$_6$) δ 167.2, 159.9, 155.4, 148.9, 136.7, 135.6, 127.6, 122.9, 121.5, 114.9, 53.4, 44.6, 34.1, 27.1, 25.9, 25.1; CI-MS (methane) (m/z): 311 [M+H]$^+$; HPLC [free base]: method C, 8.67 minutes (96.4%); method D, 12.70 minutes (97.9%); Anal. Calcd for C$_{20}$H$_{26}$N$_2$O.C$_4$H$_4$O$_4$: C, 67.59; H, 7.09; N, 6.57. Found: C, 67.5 1; H, 7.07; N, 6.54.

The trans-isomer (b) trans-4'-(3-Pyridin-2-ylpropylamino) cyclohexyl]-phenol was isolated as the maleate salt (0.54 g, 7%): mp 167–169° C.; IR (KBr): 2940, 1576, 1516 cm$^{-1}$; $^1$H NMR(300 MHz, CD$_3$OD) δ 8.49 (d, J=5 Hz, 1H), 7.80 (t, J=6 Hz, 1H), 7.36 (d, J=8 Hz, 1H), 7.30 (t, J=8 Hz, 1H), 7.03 (d, J=8 Hz, 2H), 6.70 (d, J=8 Hz, 2H), 6.25 (s, 2H), 3.21–3.09 (m, 3H), 2.93 (t, J=8 Hz, 2H), 2.54–2.53 (m, 1H), 2.30–1.90 (m, 6H), 1.65–1.46 (m, 4H); CI-MS (methane) (m/z): 311 [M+H]$^+$; HPLC [free base]: method C, 4.87 minutes (95.7%); Anal. Calcd for C$_{20}$H$_{26}$N$_2$O.C$_4$H$_4$O$_4$: C, 67.59; H, 7.09; N, 6.57. Found: C, 67.39; H, 7.13; N 6.37.

EXAMPLE 16

IUPAC: trans-N-Benzyl-N-[4-(4-hydroxyphenyl)cyclohexyl]acetamide

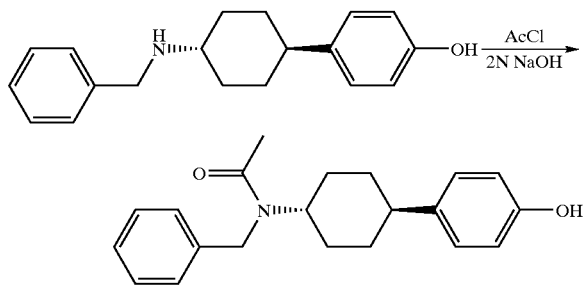

To trans-4-(4-benzylaminocyclohexyl)phenol (296 mg, 1.05 mmol) in 2N NaOH (5 mL) was added excess acetic anhydride. After 1 hour, the reaction mixture was poured into EtOAc (50 mL). The organic layer was dried (Na$_2$SO$_4$) and concentrated under reduced pressure. Purification by flash chromatography (silica, 9:4:1 CH$_2$Cl$_2$:MeOH:NH$_4$OH) gave trans-N-benzyl-N-[4-(4-hydroxyphenylcyclohexyl]acetamide (170 mg, 21%) as a 50:50 mixture of rotomers: mp 227–235° C.; IR (KBr): 3200, 2929, 1650, 1612 cm$^{-1}$; $^1$H NMR (300 MHz, DMSO-d$_6$) δ 9.10 (s, 0.5H), 9.09 (s, 0.5H), 7.36–7.17 (m, 5H), 6.97 (d, J=9 Hz, 2H), 6.65 (d, J=9 Hz, 1H), 6.64 (d, J=9 Hz, 1H), 4.57 (s, 1H), 4.51 (s, 1H), 4.42 (m, 0.5H), 3.84 (m, 0.5H), 2.42–2.39 (m, 1H), 2.21 (s, 1.5H), 1.97 (s, 1.5H), 1.75–1.47

(m, 8H); CI-MS (methane) (m/z): 324 [M+H]⁺. HPLC: method A, 8.79 minutes (97.4%); Anal. Calcd for $C_{21}H_{25}NO_2$: C, 77.99; H, 7.79; N, 4.33. Found: C, 77.61; H, 7.76; N 4.21.

EXAMPLE 17

(a) trans-N-[4-(4-Hydroxyphenyl)cyclohexyl]-N-(3-phenylpropyl)acetamide

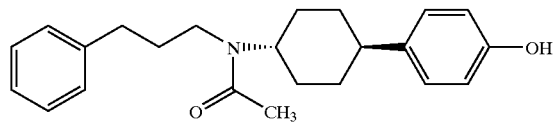

In a manner similar to Example 16, trans-4-[4-(3-phenylpropylanino)cyclohexyl]phenol was allowed to react with acetic anhydride to give trans-N-[4-(4-hydroxyphenyl) cyclohexyl]-N-(3-phenylpropyl) acetamide. Yield (90 mg, 2%): mp 175–180° C.; IR (KBr): 3240, 2929, 1620, 1590 cm⁻¹; ¹H NMR (300 MHz, DMSO-d₆) δ 9.11 (s, 1H), 7.30–7.17 (m, 5H), 7.00 (d, J=9 Hz, 2H), 6.69 (dd, J=9, 2 Hz, 2H), 3.37 (m, 1H), 3.25 (m, 4H), 2.61 (m, 2H), 2.41 (m, 1H), 2.10 (s, 3H), 1.87–1.75 (m, 4H), 1.72–1.46 (m, 4H); CI-MS (methane) (m/z): 352 [M+H]⁺; HRMS-API (m/z): [M+H]⁺ Calcd for $C_{23}H_{29}NO_2$, 352.2276. found: 352.2278. HPLC: method A, 12.08 minutes (97.3%); method B, 16.36 minutes (98.9%); Anal. Calcd for $C_{23}H_{29}NO_2 \cdot 0.75H_2O$: C, 75.67; H, 8.43; N, 3.84. Found: C, 75.40; H, 7.93; N, 3.78.

EXAMPLE 18

Trans-N-[4-(4-Hydroxyphenyl)cyclohexyl]-N-(3-phenylpropyl)carbamic acid methyl ester

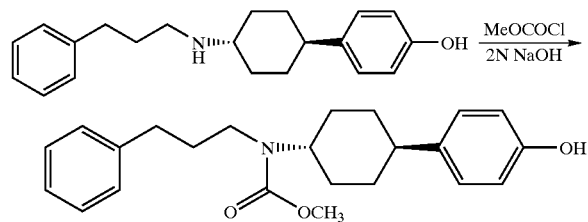

To a stirred solution of trans-4-[4-(3-phenylpropylamino) cyclohexyl]-phenol (0.40 g, 1.3 mmol) in a mixture of 2 N NaOH (5 mL) and THF (5 mL) was added methyl chloroformate (0.12 mL, 1.6 mmol). The reaction mixture was stirred at room temperature for 2 hours. Methyl chloroformate (0.05 mL, 0.65 mmol) was added and stirring continued for another 2 hours. The mixture was diluted with EtOAc (50 mL), washed with H₂O, dried (Na₂SO₄), filtered and concentrated under reduced pressure. Purification by flash chromatography (silica, 97:3 MeOH/CH₂Cl₂) gave trans-N-[4-(4-hydroxyphenyl)cyclohexyl]-N-(3-phenylpropyl)carbamic acid methyl ester, as an off-white solid (0.068 g, 14%): mp 128–133° C.; IR (KBr): 3403, 2923, 1673, 1518 cm⁻¹; ¹H NMR(300MHz, CD₃OD) δ 7.31–7.15 (m, 5H), 7.01 (d, J=8 Hz, 2H), 6.68 (d, J=8 Hz, 2H), 3.91–3.78 (m, 1H), 3.67 (s, 3H), 3.25–3.13 (m, 2H), 2.61 (t, J=8 Hz, 2H), 2.40–2.29 (m, 1H), 1.95–1.45 (m, 10H); CI-MS (methane) (m/z): 368 [M+I]⁺; HRMS-API (m/z): [M+1]⁺ Calcd for $C_{23}H_{29}NO_3$, 368.2225. found: 368.2227; HPLC: method A, 13.78 minutes (85.2%).

EXAMPLE 19

Trans-N-benzyl-N-[4-(4-hydroxyphenyl)cyclohexyl] carbamic acid methyl ester

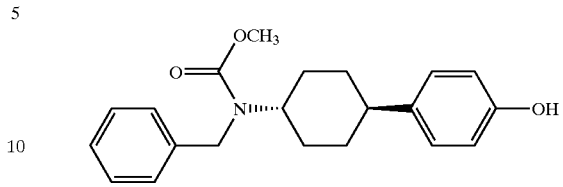

Following the procedure described in Example 18, trans-N-benzyl-N-[4-(4-hydroxyphenyl)cyclohexyl]carbamic acid methyl ester was prepared from trans-4-(4-benzylamino-cyclohexyl)phenol and methyl chloroformate yield (175 mg, 29%): mp 61–66° C.; IR (KBr): 3368, 2930, 1670, 1614 cm⁻¹; ¹H NMR (300 MHz, DMSO-d₆) δ 9.08 (s, 1H), 7.34–7.17 (m, 5H), 6.97 (d, J=9 Hz, 2H), 6.64 (d, J=9 Hz, 2H), 4.45 (s, 2 H), 3.62 (m, 1H), 3.32 (s, 3H), 2.51 (m, 1H), 1.75–1.41 (m, 8H); CI-MS (methane) (m/z): 340 [M+H]⁺; HRMS-API (m/z): [M+H]⁺ Calcd for $C_{21}H_{25}NO_3$ 340.1912; found: 340.1908. HPLC: method A, 10.30 minutes (98.6%); method B, 16.58 minutes (99.6%); Anal. Calcd for $C_{21}H_{25}NO_3 \cdot 0.125H_2O$: C, 73.82; H, 7.45; N, 4.10. Found: C, 73.72; H, 7.58; N, 3.98.

EXAMPLE 20

4-{4-[Methyl(3-phenylpropyl)amino]cyclohexyl}phenol

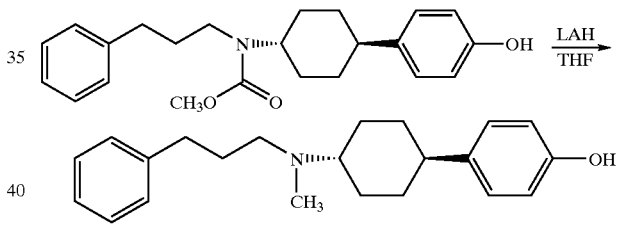

To an ice-cold, stirred solution of trans-N-[4-(4-hydroxyphenyl) cyclohexyl]-N-(3-phenylpropyl)carbamic acid methyl ester (0.30 g, 0.82 mmol) in anhydrous THF (20 mL), under a N₂ atmosphere, was added LiAlH₄ (95% powder, 0.034 g, 0.89 mmol). The reaction mixture was stirred at room temperature for 6 hours. LAH (95% powder, 0.07 mg, 1.8 mmol) was added, and stirring was continued for 14 hours. The reaction mixture was then quenched by the slow addition of H₂O (2 mL). The mixture was partitioned between EtOAc and H₂O, and the aqueous layer was extracted with EtOAc. The combined organic layers were dried (Na₂SO₄), filtered, and concentrated under reduced pressure. Purification by flash chromatography (silica, 9:1 MeOH:CH₂Cl₂) gave trans-4-{4-[methyl(3-phenylpropyl) amino]cyclohexyl}phenol (0.19 g, 70%) as an off-white solid: IR (thin film): 2931, 1613, 1515 cm⁻¹; 5 ¹H NMR (300 MHz, CD₃OD) δ 7.30–7.11 (m, 5H), 7.00 (d, J=8 Hz, 2H), 6.67 (d, J=8 Hz, 2H), 2.69–2.49 (m, 5H), 2.41–2.31 (m, 1H), 2.30 (s, 3H), 2.00–1.78 (m, 6H), 1.55–1.34 (m, 4H); CI-MS (methane) (m/z): 324 [M+H]⁺; HRMS-API (m/z): [M+H]⁺ Calcd for $C_{22}H_{29}NO$, 324.2327. found: 324.2333. HPLC: method A, 7.82 minutes (99.8%); method B, 13.89 minutes (99.7%); Anal. Calcd for $C_{22}H_{29}NO \cdot 0.25 H_2O$: C, 80.57; H, 9.07; N, 4.27. Found: C, 80.51; H, 8.83; N, 4.27.

EXAMPLE 21

Trans-N-[4-(4-Hydroxyphenyl)cyclohexyl]-3-phenylpropionamide

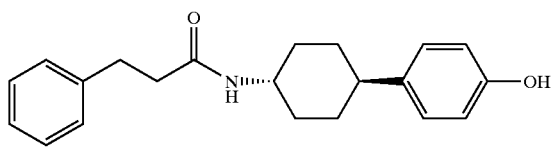

An ice-cold solution of hydrocinnamic acid (0.20 g, 1.3 mmol), Et₃N (0.20 mL, 1.4 mmol), and ethyl chloroformate (0.13 mL, 1.3 mmol) in THF (20 mL) was stirred under a N₂ atmosphere for 5 minutes. Trans-4-(4-hydroxyphenyl)cyclohexylamine 5 (0.25 g, 1.3 mmol) was added, and the mixture was stirred at room temperature for 2.5 hours. The reaction mixture was filtered, and the filtrate was concentrated under reduced pressure. Purification by flash chromatography (silica, 90:2:1 CH₂Cl₂:EtOAc:MeOH to 9:1 CH₂Cl₂:MeOH) gave IUPAC: trans-N-[4-(4-Hydroxyphenyl)cyclohexyl]-3-phenylpropionamide (140 mg, 32%) as an off-white solid: mp 201–206° C.; IR (KBr): 3298, 2931, 1638, 1514 cm⁻¹; ¹H NMR (300 MHz, CD₃OD) δ 7.30–7.13 (mn, 5H), 7.01 (d, J=9 Hz, 2H), 6.68 (d, J=9 Hz, 2H), 3.71–3.49 (m, 1H), 2.90 (t, J=7 Hz, 2H), 2.44 (t, J=7 Hz, 2H), 2.41–2.31 (m, 1H), 1.95–1.78 (m, 4H), 1.58–1.42 (m, 2H), 1.35–1.19 (m, 2H); CI-MS (methane) (m/z): 324 [M+H]⁺; HRMS-API (m/z): [M+H]⁺ Calcd for C₂₁H₂₅NO₂, 324.1963. found: 324.1962. HPLC: method A, 10.88 minutes (97.5%); method B, 13.57 minutes (99.4%); Anal. Calcd for C₂₁H₂₅NO₂.0.25H₂O: C, 76.91; H, 7.84; N, 4.27. Found: C, 77.04; H, 7.84; N, 3.88.

EXAMPLE 22

Trans-N-[4-(4-Hydroxyphenyl)cyclohexyl]-2-methyl-2-phenoxy-propionamide

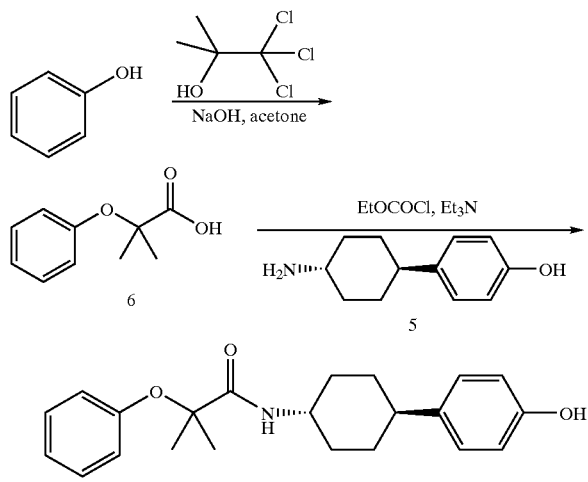

Step 1: 2-Methyl-2-phenoxypropionic acid 6 was prepared following the procedure of Corey et al., *J. Am. Chem. Soc.* 1969;91:4782. To an ice-cold, stirred suspension of powdered NaOH (3.2 g, 80 mmol) in acetone (40 mL) was added phenol (1.88 g, 20 mmol) followed by 1,1,1-trichloro-2-methyl-2-propanol hydrate (7.82 g, 40 mmol). The mixture was stirred at 0° C. for 2 hours and then at room temperature for 2 hours. The mixture was diluted with H₂O, acidified with 2N HCl, and extracted with EtOAc. The organic layer was washed with 2 N HCl, then extracted with saturated NaHCO₃ (2x). The aqueous extracts were combined, washed once with EtOAc, acidified with 2N HCl, then extracted with EtOAc (2x). The combined organic layers were washed once with saturated NaCl, dried (MgSO₄), and concentrated under reduced pressure. Purification by flash chromatography gave 6 (1.36 g, 38%): ¹H NMR (300 MHz, CDCl₃) δ 7.28 (t, J=8 Hz, 2H), 7.08 (t, J=8 Hz, 1H), 6.96 (d, J=8 Hz, 2H), 1.52 (s, 6H).

Step 2: trans-N-[4-(4-Hydroxyphenyl)cyclohexyl]-2-methyl-2-phenoxypropionamide: Reaction of trans-1-amino-4-(4-hydroxyphenyl)-cyclohexane 5 with 6, following the procedure described in Example 5, gave trans-N-[4-(4-hydroxyphenyl)cyclohexyl]-2-methyl-2-phenoxypropionamide (0.40 g, 86%): mp 114–117° C.; IR (KBr): 3355, 2930, 1654, 1515 cm⁻¹; ¹H NMR (300 MHz, CD₃OD) δ 7.30–7.22 (m, 2H), 7.05–6.80 (m, 3H), 6.90 (br d, J=8 Hz, 2H), 6.68 (br d, J=8 Hz, 2H), 3.83–3.71 (m, 1H), 2.48–2.32 (m, 1H), 2.0–1.8 (m, 4H), 1.5 (s, 6H), 1.61–1.30 (m, 4H); CI-MS (methane) (m/z): 354 [M+1]⁺; HRMS-API (m/z): [M+1]⁺ Calcd for C₂₂H₂₇NO₃, 354.2069. found: 354.2058. HPLC: method A, 12.22 minutes (95.1%); method B, 8.70 minutes (96.9%); Anal. Calcd for C₂₂H₂₇NO₃.0.25H₂O: C, 73.82; H, 7.74; N, 3.91. Found: C, 73.46; H, 7.76; N, 3.80.

EXAMPLE 23

Trans-4-[4-(3-phenylprop-2-ynylamino)cyclohexyl]phenol

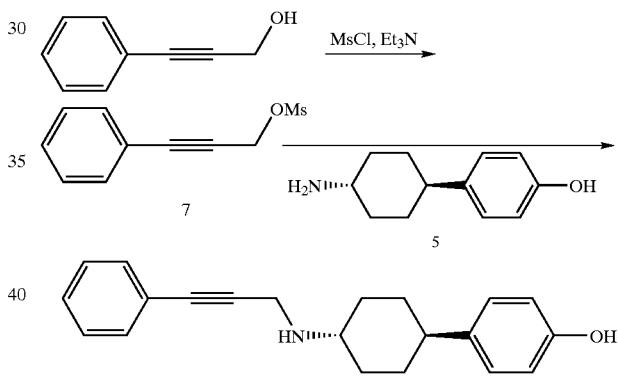

Step 1: 1-phenyl-2-propyn-1-yl methanesulfonate. To an ice-cold solution of 1-phenyl-2-propyn-1-ol (0.50 g, 3.8 mmol) in THF (15 mL), under a N₂ atmosphere, was added Et₃N (0.78 mL, 5.7 mmol), followed by methanesulfonyl chloride (0.35 mL, 4.5 mmol). After 15 minutes, the reaction mixture was diluted with EtOAc (50 mL), washed with 2N HCl, H₂O, saturated NaHCO₃, and saturated NaCl. The organic layer was dried (Na₂SO₄) and concentrated under reduced pressure to give the mesylate 7 (0.79 mg, 100%), which was used without further purification.

Step 2: trans-4-[4-(3-phenylprop-2-ynylamino) cyclohexyl]phenol. A mixture of trans-4-(4-hydroxyphenyl) cyclohexylamine 5 (0.35 g, 1.8 mmol) and mesylate 7 (0.32 g, 1.5 mmol) in THF (15 mL) was refluxed under N₂ for 17 hours. The reaction mixture was diluted with EtOAc (40 mL) and washed with H₂O, then saturated NaCl, dried (Na₂SO₄), filtered, and concentrated under reduced pressure. Purification by flash chromatography (silica, 99:1 CHCl₃:MeOH to 97:3 CHCl₃:MeOH) and conversion to the maleate salt gave trans-4-[4-(3-phenylprop-2-ynylamino) cyclohexyl]phenol (160 mg, 26%) as a white solid: mp 171–179° C.; IR (KBr): 2938, 1700, 1516cm⁻¹; ¹H NMR (300 MHz, CD₃OD) δ 7.52–7.35 (m, 5H), 7.04 (d, J=8 Hz, 2H), 6.69 (d, J=8 Hz, 2H), 6.25 (s, 2H), 4.21 (s, 2H), 3.45–3.35 (obs m, 1H) 2.52–2.42 (m, 1H), 2.31–2.20 (m, 2H), 2.05–1.60 (m, 2H), 1.67–1.48 (m, 4H); CI-MS (methane) (m/z): 306 [M+H]$^+$; HPLC: method A, 7.63 minutes (97.9%); method B, 14.01 minutes (97.6%); Anal. Calcd for $C_{21}H_{23}NO \cdot C_4H_4O_4$: C, 71.24; H, 6.46; N, 3.32. Found: C, 71.21; H, 6.51; N, 3.22.

EXAMPLE 24

Trans-4-[4-(3-phenylprop-2-ynylamino)cyclohexyl]phenol

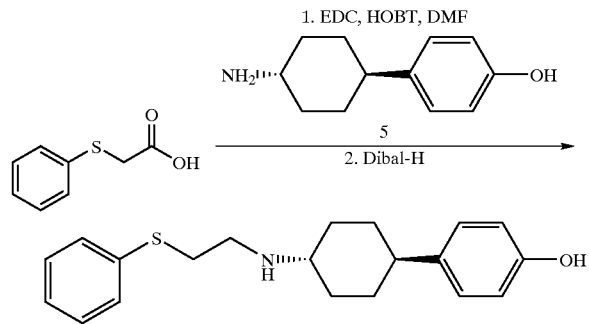

Step 1: A solution of phenylsulfanylacetic acid (0.22 g, 1.3 mmol), amine 5 (0.25 g, 1.3 mmol), EDC (0.31 g, 1.6 mmol), and HOBT (0.18 g, 1.3 mmol) in DMF (5 mL) was stirred under an $N_2$ atmosphere overnight. The reaction mixture was concentrated under reduced pressure. Purification by flash chromatography (silica, 9:1 $CH_2Cl_2$:MeOH) gave the desired amide (0.27 g, 61%): CI-MS (methane) m/z=342 [M+H]$^+$.

Step 2: To a magnetically stirred suspension of the amide (0.27 g, 0.78 mmol) in THF (5 mL), under an $N_2$ atmosphere, was added DIBAL-H (1.6 mL of a 1 M solution in THF, 1.6 mmol). The reaction mixture was stirred at room temperature for 1 hour and then heated to reflux. After 1 hour at reflux, additional DIBAL-H (1.6 mL of a 1 M solution in THF, 1.6 mL, 1.6 mmol) was added and the reaction mixture was stirred at reflux overnight. Additional DIBAL-H (0.8 mL of a 1 M solution in THF, 0.8 mmol) was added, and after 4 hours, the reaction mixture was cooled to room temperature. The reaction mixture was quenched by the slow addition of MeOH (50 mL), and the resultant mixture was heated under reflux for 15 minutes. The remaining solid was removed by filtration, and the filtrate was concentrated under reduced pressure. Purification by flash chromatography (silica, 95:5 $CH_2Cl_2$:MeOH) gave trans-4-[4-(3-phenylprop-2-ynylamino)cyclohexyl]phenol (0.11 g, 41%) as a white solid: mp 131–136° C., IR (KBr): 2921, 1611, 1592, 1514 cm$^{-1}$; $^1$H NMR (300 MHz, $CD_3OD$) δ 7.42–7.19 (m, 5H), 7.00 (d, J=9 Hz, 2H), 6.67 (d, J=9 Hz, 2H), 3.08 (t, J=7 Hz, 2H), 2.83 (t, J=7 Hz, 2H) 2.51 (tt, J=15, 3 Hz, 1H), 2.39 (tt, J=15, 3 Hz, 1H), 1.98 (br d, J=12 Hz, 2H), 1.83 (br d, J=12 Hz, 2H), 1.50 (dddd, J=15,15,15,3, 2H), 1.22 (dddd, J=15,15,15,3 Hz, 2H): CI-MS (methane) (m/z): 328 [M+H]$^+$; HRMS-API (m/z): [M +H]$^+$ Calcd for $C_{20}H_{25}NOS$, 328.1735. found: 328.1746. HPLC: method A, 7.69 minutes (97.9%); method B, 14.13 minutes (99.7%); Anal. Calcd for $C_{20}H_{25}NOS$: C, 72.36; H, 7.74; N, 4.22. Found: C, 72.70; H, 7.73; N, 4.21.

EXAMPLE 25

Trans-4-[4-(2-phenylaminoethylamino)cyclohexyl]phenol

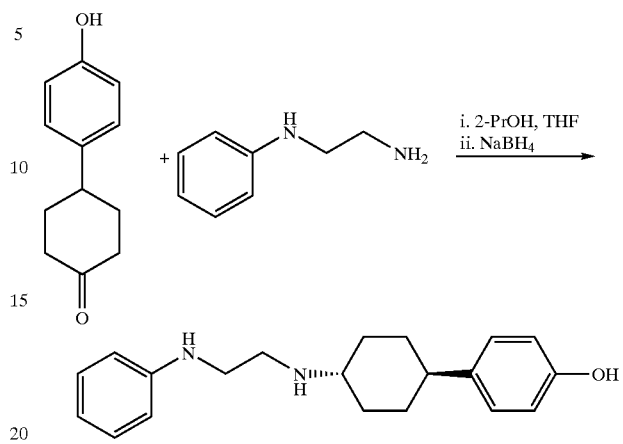

To a stirred solution of 4-(4-hydroxyphenyl) cyclohexanone (1.0 g, 5.3 mmol) in a mixture of 2-propanol (40 mL) and THF (20 mL) was added N-phenylethylenediamine (0.72 g, 5.3 mmol) and 3 Å molecular sieves. After 3 hours, sodium borohydride (0.27 g, 7.3 mmol) was added, and the reaction mixture was stirred overnight. The reaction mixture was quenched with MeOH, filtered through celite, and the filtrate was concentrated under reduced pressure. The product was purified by flash chromatography (silica, 95:5 $CH_2Cl_2$:MeOH) and converted to a maleate salt. Recrystallization from MeOH/$Et_2O$ gave trans-4-[4-(2-phenylamino-ethylamino)cyclohexyl]phenol (0.31 g, 14%), as yellow solid: mp 180–184° C.; IR (KBr): 3368, 2945, 2863, 1516 cm$^{-1}$; $^1$H NMR (500 MHz, DMSO-$d_6$) δ 9.14 (s, 1H), 8.40 (br s, 2H), 7.15–7.00 (m, 4H), 6.70–6.55 (m, 5H), 6.02 (s, 2H), 5.65 (br s, 1H), 3.40–3.25 (m, 2H), 3.20–3.10 (m, 3H), 2.45–2.40 (m, 1H), 2.20–2.10 (m, 2H), 1.90–1.80 (m, 2H), 1.50–1.35 (m, 4H); API-MS (m/z): 311 [M+H]$^+$; HPLC: method A, 7.38 minutes (99.1%); method B, 13.29 minutes (99.1%); Anal. Calcd for $C_{20}H_{26}N_2O \cdot C_4H_4O_4$: C, 67.59; H, 7.09; N, 6.57. Found: C, 67.38; H, 7.01; N 6.55.

EXAMPLE 26

Trans-4-{4-[N-ethyl-N-(3-phenylpropyl)amino]cyclohexyl) phenol.

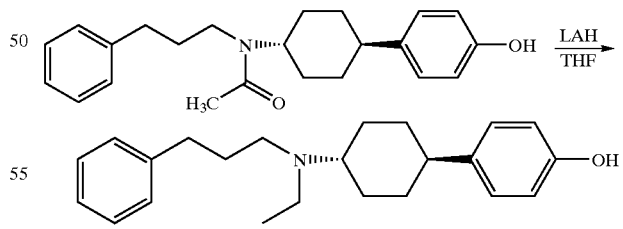

To a stirred solution of trans-N-[4-(4-hydroxyphenyl) cyclohexyl]-N-(3-phenylpropyl)acetamide (282 mg, 0.80 mmol) in anhydrous THF (5 mL) was added LiAlH$_4$ (1.2 mL of a 1M solution in $Et_2O$, 1.2 mmol). After 18 hours, the reaction was quenched by addition of a mixture of $H_2O$ (2 mL), 2N NaOH (4 mL), and saturated NaCl (2 mL). The resulting mixture was diluted with $Et_2O$ (100 mL) and the resulting mixture was filtered. The filtrate was dried ($Na_2SO_4$) and concentrated under reduced pressure. Purification by flash chromatography (90:9:1 $CH_2Cl_2$:MeOH:$NH_4OH$) gave trans-4-{4-[N-ethyl-N-(3-phenylpropyl)-amino]cyclohexyl}phenol (130 mg, 48%) as a white solid: mp 192–194° C.; IR (KBr): 3197, 2939, 1614, 1516 cm$^{-1}$; $^1$H NMR (500 MHz, DMSO-d$_6$) δ 9.16 (br s, 1H), 7.35–7.23 (m, 5H), 7.02 (d, J=8 Hz, 2H), 6.70 (d, J=8 Hz, 2H), 3.35–3.12 (m, 5H), 2.68 (q, J=5, 2 Hz, 2H), 2.42 (tt, J=9, 2 Hz, 1H), 2.12 (br d, J=9 Hz, 2H), 2.10 (m, 2H), 1.87 (br d, J=9 Hz, 2H), 1.63 (dddd, J=9, 9, 9, 2 Hz, 2H), 1.53 (dddd, J=9, 9, 9, 2 Hz, 2H), 1.27 (t, J=5 Hz, 3H); CI-MS (methane) (m/z): 338 [M+H]$^+$; HPLC: method A, 8.80 minutes (97.8%); method B, 10.66 minutes (99.9%); Anal. Calcd for $C_{23}H_{31}NO·HCl·0.125H_2O$: C, 73.43; H, 8.64; N, 3.72. Found: C, 73.36; H, 8.75; N, 3.56.

EXAMPLE 27

Trans-4-{4-[N-isopropyl-N-(3-phenylpropyl)amino]cyclohexyl}phenol

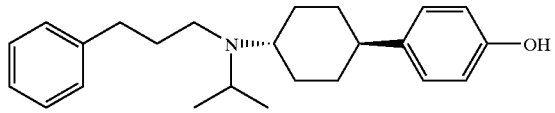

To a stirred solution of trans-4-[4-(3-phenylpropyl amino)cyclohexyl]-phenol and acetone (2 mL) in a 2:1 mixture of THF:MeOH (10 mL) was added sodium cyanoborohydride (153 mg, 2.42 mmol). The reaction mixture was heated to 60° C. and the acidity was maintained by the addition of acetic acid. The mixture was stirred overnight, quenched with 2N NaOH and concentrated under reduced pressure. Purification by flash chromatography (90:9:1 $CH_2Cl_2$:MeOH:$NH_4OH$) gave trans-4-{4-[N-isopropyl-N-(3-phenylpropyl) amino]cyclohexyl}phenol (130 mg, 48%), as a white solid: mp 146–154° C.; IR (KBr): 3198, 2941, 1613 cm$^{-1}$; $^1$H NMR (500 MHz, DMSO-d$_6$) δ or s δ 7.32–7.21 (m, 5H), 6.98 (d, J=8 Hz, 2H), 6.66 (d, J=8 Hz, 2H), 3.67 (m, 1H), 3.28 (m, 2H), 3.10 (m, 2H), 2.66 (m, 2H), 2.48 (m, 1H), 2.04 (m, 1H), 2.02 (m, 2H), 1.84 (m, 2H), 1.83 (m, 2H), 1.49 (m, 2H), 1.24 (d, J=8 Hz, 3H), 1.19 (d, J=8 Hz, 3H); CI-MS (methane) (m/z): 352 [M+H]$^+$; HRMS-API (m/z): [M+H]$^+$ Calcd for $C_{24}H_{33}NO$, 352.2640. found: 352.2637. HPLC: method A, 6.37 minutes (95.3%); method B, 10.85 minutes (100%); Anal. Calcd for $C_{24}H_{33}NO·HCl·0.5$ NaCl: C, 69.09; H, 8.21; N, 3.36. Found: C, 69.33; H, 8.32; N, 3.22.

EXAMPLE 28

Trans-4-{4-[3-(4-methoxyphenyl)propylamino]cyclohexyl}phenol

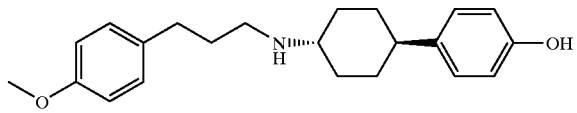

To a stirred solution of amine 5 (0.30 g, 1.6 mmol) and 3-(4-methoxyphenyl)propionaldehyde (0.26 g, 1.6 mmol) in a mixture of MeOH (5 mL) and 1,2-dichloroethane (10 mL) was added sodium triacetoxyborohydride (0.47 g, 2.2 mmol). After 4 hours, the solvents were removed under reduced pressure. The product was partitioned between EtOAc and $H_2O$ and the mixture shaken until most of the solids dissolved. The organic solution was washed with saturated $NaHCO_3$, filtered, then washed with a mixture of 1N HCl containing a little saturated NaCl. A precipitate formed which was collected by filtration. Recrystallization from MeOH gave the HCl salt, trans-4-{4-[3-(4-methoxyphenyl) propylamino]cyclohexyl}phenol (0.22 g, 62%), as a white solid: mp 235–241° C.; IR (KBr): 1514, 1249, 1033 cm$^{-1}$; $^1$H NMR (500 MHz, DMSO-d$_6$) δ 9.15 (s, 1H), 8.79 (br s, 2H), 7.16, 7.00, 6.88, and 6.67 (all d, J=8.4 Hz, 2H), 3.74 (s, 3H), 3.03 (m, 1H), 2.88 (m, 2H), 2.60 (t, J=7.6 Hz, 2H), 2.37 (m, 1H), 2.12 (br d, J=12.1 Hz, 2H), 2.12 (tt, J=7.6, 7.6 Hz, 2H), 1.83 (br d, J=12.3 Hz, 2H), 1.53–1.35 (m, 4H); CI-MS (methane) (m/z): 340 [M+H]$^+$; HRMS-API (m/z): [M+H]$^+$ Calcd for $C_{22}H_{29}NO_2$, 340.2276. found: 340.2273. HPLC: method A, 7.76 minutes (99.4%); method B, 14.04 minutes (99.9%); Anal. Calcd for $C_{22}H_{29}NO_2·HCl·0.125$ $H_2O$: C, 69.87; H, 8.06; N, 3.70. Found: C, 69.77; H, 7.71; N, 3.60.

EXAMPLE 29

4-{4-[benzyl(3-phenylpropyl)amino]cyclohexyl}phenol

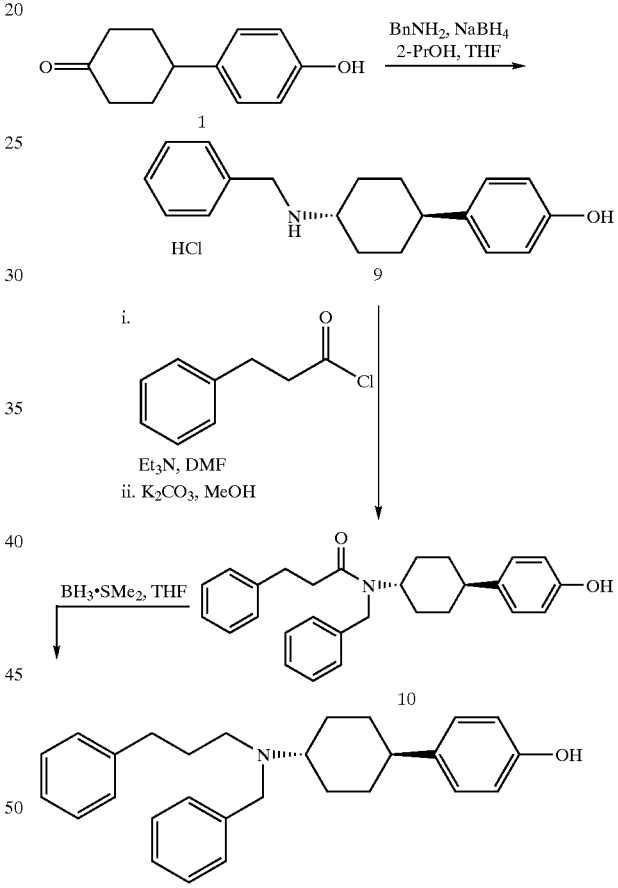

Step 1: A mixture of 1 (10 g, 0.05 mol) and benzylamine (5.75 mL, 0.05 mol) in toluene (150 mL) was heated under Dean-Stark conditions for 3 hours. The solution was cooled to room temperature and then concentrated under reduced pressure. 2-PrOH (100 mL) was added, and the mixture was heated under reflux until all of the solid dissolved. The solution was cooled in an ice bath and sodium borohydride (3 g, 0.079 mol) was added. The mixture was stirred at room temperature for 1 hour. Methanol (100 mL) was added, and stirring was continued for 1 hour. The mixture was acidified with 2N HCl and then shaken between water and $Et_2O$. The trans-isomer 9 precipitated from solution, yield (9.35 g, 59%): $^1$H NMR (500 MHz, DMSO-d$_6$) δ 9.26 (br s, 2H), 9.14 (br s, 1H), 7.60 (dd, J=8, 2 Hz, 2H), 7.40–7.48 (m, 3H), 7.01 (d, J=9 Hz, 2H), 6.68 (d, J=9 Hz, 2H), 4.17 (t, J=6 Hz, 2H), 3.05 (m, 1H), 2.49 (tt, J=12, 4 Hz, 1H), 2.25 (br d, J=11 Hz, 2H) 1.85 (br d, J=12 Hz, 2H), 1.61 (dddd, J=12, 12, 12, 3 Hz, 2H), 1.42 (dddd, J=12, 12, 12, 3 Hz, 2H).

Step 2: To a solution of hydrocinnamic acid (1.0 g, 6.6 mmol) in CH$_2$Cl$_2$ (20 mL) was added DMF (5 drops) and oxalyl chloride (0.7 mL, 8.0 mmol). After stirring for 30 minutes, DMF (10 mL) was added slowly. When the vigorous evolution of gas subsided, the CH$_2$Cl$_2$ was removed under reduced pressure. Compound 9 (1.0 g, 3.2 mmol) and triethylamine (1.7 mL, 12.2 mmol) were added, and the mixture was heated to 80° C. After 1 hour, triethylamine (1.0 mL, 7.2 mmol) was added, and heating was continued for 1 hour. The reaction mixture was cooled to room temperature and partitioned between EtOAc and 2N HCl. The organic layer was washed with 2N HCl, water, saturated NaHCO$_3$, and saturated NaCl, dried (MgSO$_4$), and concentrated under reduced pressure. The residue was taken up in MeOH (20 mL), K$_2$CO$_3$ (0.5 g) added, and the mixture stirred at room temperature overnight. The reaction mixture was diluted with water and EtOAc, and then acidified with 2N HCl. The organic layer was washed with 2N HCl, sat. NaHCO$_3$, and sat. NaCl, dried (MgSO$_4$), and concentrated under reduced pressure. Purification by flash chromatography (4:1 to 3:1 to 2:1 hexanes:EtOAc) gave 10 (0.86 g, 66%) as a mixture of isomers: $^1$H NMR (300 MHz, CDCl$_3$) δ 6.70–7.40 (m, 14H), 4.63 (m, 1H), 4.62 and 4.40 (both s, 2H), 3.73 (m, 1H), 3.09 and 2.98 (both t, J=7 Hz, 2H), 2.70 and 2.55 (both t, J=7 Hz, 2H), 2.33 (m, 1H), 1.30–1.95 (m, 8H).

Step 3: A solution of amide 10 (0.86 g, 2 mmol) and BH$_3$.SMe$_2$ (2 mL of a 2 M solution in THF, 4 mmol) in THF (20 mL) was stirred at room temperature overnight and then heated under reflux for 15 min. After cooling to room temperature, MeOH (20 mL) was added, and the mixture was concentrated under reduced pressure. MeOH (20 mL) was added, followed by concentrated HCl (0.5 mL), and the mixture was concentrated under reduced pressure. The residue was twice taken up in MeOH (20 mL) and re-concentrated. The product was re-crystallized from MeOH (5 mL). The product was dissolved in a hot MeOH:CHCl$_3$ mixture and the resultant solution neutralized with dilute NaHCO$_3$. The free amine was extracted into CHCl$_3$. The organic solution was dried (MgSO4) and concentrated under reduced pressure. Purification by flash chromatography (silica, eluent CHCl$_3$ to 98:2 CHCl$_3$:MeOH), followed by conversion to the HCl salt, gave 4-(4-[benzyl-(3-phenylpropyl)amino]-cyclohexyl}phenol (0.62 g, 68%), as a white solid: mp 259–264° C.; IR (KBr): 1613, 1515, 1225 cm$^{-1}$; $^1$H NMR (500 MHz, DMSO-d$_6$) δ 9.58 (br s, 1H), 9.12 (br s, 1H), 7.57 (dd, J=6, 2 Hz, 1H), 7.46 (d, J=2 Hz, 1H), 7.45 (d, J=6, 1H), 7.28 (t, J=7 Hz, 2H), 7.19 (t, J=7 Hz, 1H), 7.16 (d, J=7 Hz, 2H), 7.00 (d, J=9 Hz, 2H), 6.68 (d, J=8 Hz, 2H), 4.46 (dd, J=13, 4 Hz, 1H), 4.24 (dd, J=13, 7 Hz, 1H), 3.35–3.40 (m, 1H), 3.12–3.20 (m, 1H), 2.99 (br t, J=11 Hz, 1H), 2.40–2.60 (m, 3H), 2.17 (d, J=11 Hz, 2H), 1.96–2.06 (m, 1H), 1.88 (d, J=11 Hz, 2H), 1.68–1.86 (m, 3H), 1.42–1.52 (m, 2H); CI-MS (methane) (m/z): 400 [M+H]$^+$; HPLC: method A, 7.52 min (96.5%); method B, 11.25 min (>99%); Anal. Calcd for C$_{28}$H$_{33}$NO.HCl: C, 77.13; H, 7.86; N, 3.21. Found: C, 76.78; H, 8.09; N, 3.14.

EXAMPLE 30

4-{4-[methyl(2-phenoxyethyl)amino]cyclohexyl}phenol

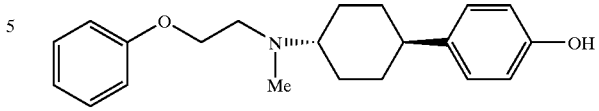

To a stirred solution of 4-[4-(2-phenoxyethylamino) cyclohexyl]phenol (0.35 g, 1.13 mmol) in a mixture of MeOH (10 mL), water (1 mL) and CH$_2$Cl$_2$ (5 mL) was added p-formaldehyde (0.17 g, 5.62 mmol). The reaction mixture was stirred for 2 hours, sodium triacetoxyborohydride (0.33 g, 1.58 mmol) was added and stirring was continued overnight. Solid NaOH was added, until the solution turned clear. Silica gel was added, and the solvents were removed under reduced pressure. Purification by flash chromatography (10:1 CH$_3$Cl:MeOH) gave 4-{4-[methyl(2-phenoxyethyl)amino]cyclohexyl}-phenol (264 mg, 72%) as a white solid: mp 216–220° C.; IR (KBr): 3149, 2936, 1599 cm$^{-1}$; $^1$H NMR (500 MHz, DMSO-d$_6$) δ 9.14 (br s, 1H), 7.34 (dd, J=9, 9 Hz, 2H), 7.00 (d, J=9 Hz, 5H), 6.68 (d, J=9 Hz, 2H), 4.42 (br s, 2H), 3.61–3.33 (m, 3H), 2.82 (s, 3H), 2.92 (t, J=5 Hz, 2H), 2.49 (tt, J10, 2 Hz, 1H), 2.19 (dd, J=10, 2 Hz), 1.88 (br d, J=10 Hz, 2H), 1.74 (dddd, J=10, 10, 10, 2 Hz, 2H), 1.47 (dddd, J=10, 10, 10, 2 Hz, 2H); CI-MS (methane) (m/z): 326 [M+H]$^+$; HPLC: method A, 5.64 min (95.3%); method B, 9.63 min (99.2%); Anal. Calcd for C$_{24}$H$_{33}$NO.HCl: C, 69.69; H, 7.80; N, 3.87. Found: C, 69.44; H, 7.81; N, 3.80.

EXAMPLE 31

2-aminomethyl-4-{4-[ethyl(3-phenylpropyl)amino] cyclohexyl}phenol

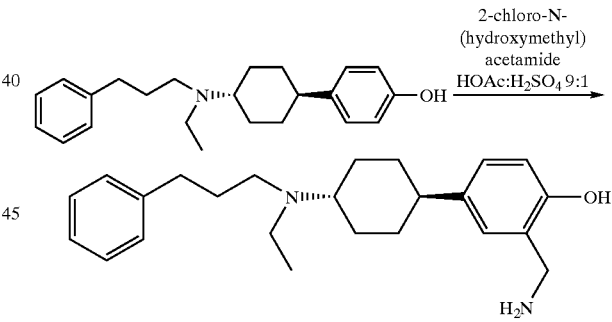

(Stokker G. E., Deana A. A., deSolms S. J., Schultz E. M., Smith R. L., Cragoe E. J. Jr., *J. Med Chem.,* 1980;23:1414).

A mixture of HOAc and H$_2$SO$_4$ (1 mL, 9:1, v:v) was cooled to 10° C. 4-{4-[ethyl(3-phenylpropyl)amino] cyclohexyl}phenol (200 mg, 0.53 mmol) and 2-chloro-N-(hydroxymethyl)acetamide (66 mg, 0.53 mmol) were added portionwise. The reaction mixture was warmed to room temperature and stirred for 16 hours. The mixture was poured onto ice (1 g) and water (10 mL) was added. After concentration under reduced pressure, a mixture of EtOH and HCl (6.5 mL, 10:3, v:v) was added, and the mixture was heated under reflux for 1.5 hours. The mixture was cooled to room temperature and concentrated under reduced pressure. Purification by flash chromatography (silica, 90:10:0.5 CH$_2$Cl$_2$:MeOH:NH$_4$OH), followed by formation of the HCl salt, gave 2-aminomethyl-4-{4-[ethyl(3-phenylpropyl) amino]cyclohexyl}phenol (65 mg, 28%), as a yellow solid:

mp 168–173° C.; IR (KBr): 2940, 1510, 1453 cm$^{-1}$; $^1$H NMR (500 MHz, DMSO-d$_6$) δ 10.16 (br s, 1H), 9.96 (s, 1H), 8.1 (br s, 2H), 7.35–7.17 (m, 6H), 7.06 (dd, J=8 Hz, 1H), 6.85 (d, J=8 Hz, 1H), 3.90 (br d, J=5 Hz, 2H), 3.45–2.98 (m, 4H), 2.71–2.65 (m, 2H), 2.52–2.39 (m, 2M), 2.19–2.10 (m, 2H), 2.10–2.05 (m, 2H), 1.90–1.83 (m, 2H), 1.70–1.49 (m, 4H), 1.27 (t, J=7 Hz, 3H) API-MS (methane) (m/z): 367 [M+H]$^+$; HRMS-API (m/z): [M+H]$^+$ Calcd for C$_{24}$H$_{34}$N$_2$O, 367.2749. found: 367.2741. Anal. Calcd for C$_{24}$H$_{34}$N$_2$O.02HCl.H$_2$O: C, 64.93; H, 8.29; N, 6.31. Found: C, 64.90; H, 8.53; N, 6.09.

Electrophysiological Assays at NMDA Receptor Subunits

Preparation of RNA. cDNA clones encoding the NR1A, NR2A, NR2B, and NR2C rat NMDA receptor subtypes were used (see Moriyoshi et al., Nature (Lond.), 1991;354:31–37); Kutsuwada et al., Nature (Lond.), 1992;358: 36–41; Monyer et al., Science (Washington, D.C.), 1992;256:1217–1221; Ikeda et al., FEBS Lett., 1992;313:34–38; Ishii et al., J. Biol. Chem. 1993;268:2836–2843 for details of these clones or their mouse homologs). The clones were transformed into appropriate host bacteria and plasmid preparations were made with conventional DNA purification techniques. A sample of each clone was linearized by restriction enzyme digestion of cRNA was synthesized with T3 RNA polymerase. The cRNA was diluted to 400 ng/μL and stored in 1 μL aliquots at −80° C. until injection.

The Xenopus Oocyte Expression System. Mature female Xenopus laevis were anaesthetized (20–40 minutes) using 0.15% 3-aminobenzoic acid ethyl ester (MS-222), and 2 to 4 ovarian lobes were surgically removed. Oocytes at developmental stages IV–VI (Dumont J. N., J. Morphol., 1972;136:153–180) were dissected from the ovary still surrounded by enveloping ovarian tissues. Follicle-enclosed oocytes were micro-injected with 1:1 mixtures of NR1A:NR2A, 2B or 2C.; injecting 1 to 10 ng of RNA encoding each receptor subunit. NR1A encoding RNA was injected alone at ~20 ng. Oocytes were stored in Barth's medium containing (in mM): NaCl, 88; KCl, 1; CaCl$_2$, 0.41; Ca (NO$_3$)$_2$, 0.33; MgSO$_4$, 0.82; NaHCO$_3$, 2.4; HEPES 5, pH 7.4, with 0.11 mg/ml gentamicin sulphate. While oocytes were still surrounded by enveloping ovarian tissues, the Barth's medium was supplemented with 0.1% bovine serum. Oocytes were defolliculated 1 to 2 days following injections by treatment with collagenase (0.5 mg/mL Sigma Type I for 0.5–1 hour)-(Miledi and Woodward, J. Phsyiol. (Lond.), 1989;416:601–621) and subsequently stored in serum-free medium.

Electrical recordings were made using a conventional two-electrode voltage clamp (Dagan TEV-200) over periods ranging between 3 to 21 days following injection (Woodward et al., Mol. Pharmacol., 1992;41:89–103). Oocytes were placed in a 0.1 mL recording chamber continuously perfused (5–15 mL min$^{-1}$) with frog Ringer's solution containing (in mM): NaCl, 115; KCL, 2; BaCl$_2$, 1.8; HEPES, 5; pH 7.4. Drugs were applied by bath perfusion. Using oocytes expressing different subunit combinations of NMDA receptor, NMDA currents were activated by co-application of glutamate (100 μM) and glycine (1–100 μM). Inhibitory potency of the novel antagonists was assessed on responses elicited by fixed concentrations of glutamate and glycine, by measuring reductions in current induced by progressively increasing concentrations of antagonist.

Concentration-inhibition curves were fit with Equation 1.

$$I/I_{control} = 1/(1+([antagonist]/10^{-pIC_{50}})^n)$$  Eq. 1

In which I$_{control}$ is the current evoked by agonists alone, pIC$_{50}$ = −log IC$_{50}$, IC$_{50}$ is the concentration of antagonist that produced half maximal inhibition, and n is the slope factor (De Lean et al., Am. J. Physiol., 1978;235:E97–102). For incomplete curves analysis by fitting was unreliable and IC$_{50}$ values were calculated by simple regression over linear portions of the curves (Origin: Microcal Software).

The electrophysiological assay results are set forth in Tables 1–4.

6-OHDA-lesioned Rat Assay:

6-Hydroxydopamine-lesioned rats were used (see Ungerstedt U., Arbuthnott G. W., Quantitative recording of rotational behavior in rats after 6-hydroxy-dopamine lesions of the nigrostraiatal dopamine system. Brain Res., 1971 ;24(3) :485–93). Adult male Sprague-Dawley rats were anesthetized with chloral hydrate and unilateral lesions of the nigrostriatal dopamine system were accomplished by infusion of 8 μg of 6-hydroxydopamine HBr (6-OHDA) into the right medial forebrain bundle. Rats were pretreated 30 minutes before surgery with desipramine HCl 25 mg/kg intraperitoneally (IP) to protect noradrenegic neurons, and pargyline 25 mg/kg IP to potentiate the effects of 6-OHDA. A minimum of 3 weeks after surgery, the rotational behavior induced by apomorphine HCL 50 μg/kg subcutaneously (SC) was assessed. Only rats demonstrating more than 100 contraversive turns/hour to apomorphine were used for the present experiments.

Rotational behavior was measured using an automatic rotometer system (Rotorat Rotational Activity System, MED Associates, Georgia, Vt.). Anti-parkinsonian activity was assessed as the ability of the compound to potentiate the contraversive rotation induced by L-DOPA methyl ester, 10 mg/kg SC, over a 6-hour period. Experiments were conducted using a crossover paradigm where each rat received either a vehicle plus L-DOPA, or the test compound plus L-DOPA, in randomized order. Rats were tested at 7-day intervals. In experiments in which the compound was tested orally, rats were food deprived for 16 hours. Statistical analysis between treatment groups were performed using a paired t-test. The results were reported in Table 1 as the minimum effective dose (MED) of compound required to produce a statistically-significant increase in total contraversive rotations compared to rats receiving L-DOPA only.

TABLE 1

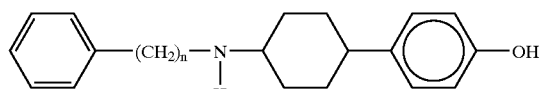

| Example No. | N | cis/trans | NR1a/NR2B Oocyte IC$_{50}$ (μM) |
|---|---|---|---|
| 2b | 3 | trans | 0.034 |
| 1b | 4 | trans | 0.035 |
| 2a | 3 | cis | 0.60 |
| 9 | 5 | trans | 0.35 |
| 3b | 2 | trans | 0.45 |
| 3a | 2 | cis | 0.83 |
| 1a | 4 | cis | 0.90 |
| 4b | 1 | trans | 43.00 |
| 4a | 1 | cis | 70.00 |

TABLE 2

![structure: phenyl-Z-N(R)-cyclohexyl-phenyl-OH]

| Example No. | Z | R | cis/trans | IC$_{50}$ ($\mu$M) |
|---|---|---|---|---|
| 11b | —O—CH$_2$CH$_2$CH$_3$ | H | trans | 0.02 |
| 23 | —C≡C—CH$_2$CH$_3$ | H | trans | 0.05 |
| 21 | —CH$_2$CH$_2$C(O)CH$_2$CH$_3$ | H | trans | 0.07 |
| 6b | —CH$_2$CH(CH$_3$)CH$_3$ (isobutyl) | H | trans | 0.10 |
| 6a | —CH$_2$CH(CH$_3$)CH$_3$ (isobutyl) | H | cis | 0.60 |
| 11a | —O—CH$_2$CH$_2$CH$_3$ | H | cis | 2.0 |
| 13 | (S)-sec-butyl | H | trans | 16 |
| 22 | —CH$_2$OC(CH$_3$)$_2$C(O)CH$_3$ | H | trans | 301 |
| 24 | —S—CH$_2$CH$_2$CH$_3$ | H | trans | 0.04 |
| 6c | (R)-2-methylbutyl | H | trans | 0.06 |
| 6d | (S)-2-methylbutyl | H | trans | 0.07 |
| 25 | —N(H)CH$_3$ ethyl chain | H | trans | 0.05 |
| 10b | —CH(CH$_2$OH)CH$_2$CH$_3$ | H | trans | 5.0 |
| 10a | —CH(CH$_2$OH)CH$_2$CH$_3$ | H | cis | 29 |
| 16 | CH$_2$ | C(O)CH$_3$ | trans | 200 |
| 18 | —CH$_2$CH$_2$CH$_2$CH$_2$— | CH$_3$ | trans | 0.05 |
| 17 | (CH$_2$)$_3$ | C(O)CH$_3$ | trans | 4.4 |
| 19 | CH$_2$ | C(O)CH$_3$ | trans | 240 |

TABLE 3

Ar—(CH$_2$)$_n$—NH-cyclohexyl-phenyl-OH

| Example No. | N | Ar | cis/trans | NR1a/NR2B Oocyte IC$_{50}$ ($\mu$M) |
|---|---|---|---|---|
| 15b | 3 | 2-pyridinyl | trans | 0.53 |
| 14b | 3 | 3-pyridinyl | trans | 0.75 |
| 12b | 3 | 4-pyridinyl | trans | 2.1 |
| 15b | 3 | 2-pyridinyl | cis | 11.5 |
| 14b | 3 | 3-pyridinyl | cis | 24 |
| 12b | 3 | 4-pyridinyl | cis | 60 |
| 7b | 1 | 3-pyridinyl | trans | 100 |
| 7a | 1 | 3-pyridinyl | cis | 135 |

TABLE 4

Ar—(CH$_2$)$_n$—NH-cyclohexyl-phenyl-OH

| Example No. | N | Ar | Cis/Trans | NR1a/NR2B Oocyte IC$_{50}$ ($\mu$M) | Alpha 1 cocn IC$_{50}$ ($\mu$M) | D2 Raclopride IC$_{50}$ ($\mu$M) |
|---|---|---|---|---|---|---|
| 28 | 3 | 4-methoxy phenyl | Trans | 0.07 | 2.3 | 2.97 |
| 8b | 2 | 4-methoxy phenyl | Trans | 0.24 | 5.10 | 1.90 |
| 5b | 2 | 4-fluoro phenyl | Trans | 0.75 | | |
| 5a | 2 | 4-fluoro phenyl | Cis | 1.2 | 10 | 2.7 |
| 8a | 2 | 4-methoxy phenyl | Cis | 2.4 | 9.20 | 5.00 |

While the forms of the invention exemplified herein such as, for example, the named species of Formulas I–IV, and the recitation of treatment of Parkinson's constitute presently preferred embodiments, many others are possible. It is not intended that said recited species of Formulas I–IV and preferred methods of use should, in any manner, limit or restrict the invention from the full scope claimed herein. It is not intended herein to name all of the possible equivalent forms or ramifications of the invention. It is understood that the terms used herein are merely descriptive, rather than limiting. For example, the term "Parkinson's disease" is merely descriptive, and not limiting, of the term "neurodegenerative disease."

What is claimed is:

1. A compound of Formula I

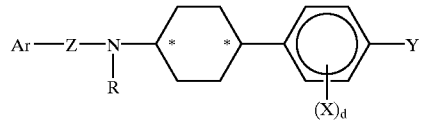

or a pharmaceutically acceptable salt thereof wherein:

Ar is substituted 1 to 3 times or Unsubstituted aryl or substituted 1–3 times or unsubstituted heteroaryl, which heteroaryl is from 5 to 14 atoms having from 1 to 2 heteroatoms selected from N, O, and S wherein the substituents are selected from the groups F, Cl, Br, I, OH, NH$_2$, SH, CN, NO$_2$, OCH$_3$, OC(O)CH$_3$, CF$_3$, OCH$_2$CH$_2$OH, NHC(O)CH$_3$, NHCH$_3$, or N(CH$_3$)$_2$;

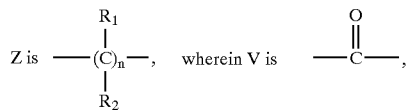

d is an integer of from 1 to 2;

q is an integer from 0 to 6;

R$_1$ and R$_2$ are independently selected from the coup consisting of hydrogen, alkyl, OH, hydroxyalkyl, aminoalkyl, aralkyl, or N(R$_4$)(R$_5$) Wherein R$_4$ and R$_5$ are independently selected from hydrogen, alkyl, aralkyl, heteroaryl, heteroarylalkyl, aminoalkyl, hydroxyalkyl and thioalkyl;

R is hydrogen, alkyl, C(O)R$_6$, C(O)OR$_6$, C(O)NHR$_6$, aralkyl, hydroxyalkyl, aminoalkyl, amino(hydroxy)alkyl, or carboxyalkyl, wherein R$_6$ is alkyl or aralkyl;

Y is OH;

X is independently selected from hydrogen or an electron withdrawing group; and

* denotes cis or trans or a mixture thereof.

2. A compound according to claim 1 wherein:

X is independently selected from hydrogen or an electron withdrawing group selected from the group consisting of halogen, intro, cyano, aminoalkyl, CF$_3$, C(O)CH$_3$, and haloalkyl.

3. A compound according to claim 1 wherein:

Ar is unsubstituted or substituted phenyl;

X is independently selected from hydrogen or an electron withdrawing group selected from the group consisting of halogen, nitro, cyano, aminoalkyl, CF$_3$, C(O)CH$_3$, and haloalkyl; and

* denotes trans.

4. A compound according to claim 1 wherein:

Ar is unsubstituted or substituted phenyl;

Z is as defined in claim 1 and further a group whereby Ar and the nitrogen atom in Formula I are separated by from 2 to 4 atoms;

X is independently selected from hydrogen or an electron withdrawing group selected from the group consisting of halogen, nitro, cyano, aminoalkyl, CF$_3$, C(O)CH3, and haloalkyl; and

* denotes trans.

5. A compound according to claim 1 selected from:

N-[4-(4-Hydroxyphenyl)cyclohexyl]-3-phenylpropionamide; and

N-[4-(4-Hydroxyphenyl)cyclohexyl]-2-methyl-2-phenoxypropionamide.

6. A compound according to claim 1 wherein:

Ar is unsubstituted or substituted phenyl;

X is independently selected from hydrogen or an electron withdrawing group selected from the group consisting of halogen, nitro, cyano, aminoalkyl, CF$_3$, C(O)CH$_3$, and haloalkyl; and

* denotes cis.

7. A pharmaceutical composition comprising a pharmaceutically acceptable carrier or diluent and a therapeutically effective amount of at least one compound of claim 1.

8. A pharmaceutical composition according to claim 7, further comprising a dopamine agonist or precursor thereof.

9. A method for treating disorders selected from stroke, cerebral ischemia, cerebral trauma, Parkinson's disease, anxiety, convulsions, opioid tolerance or withdrawal or chronic pain in a mammal suffering thereof which comprises administering in unit dosage form at least one compound.

10. A method according to claim 9, wherein the disorder is Parkinson's disease.

* * * * *